(12) United States Patent
Verdant et al.

(10) Patent No.: US 11,448,585 B2
(45) Date of Patent: Sep. 20, 2022

(54) ACOUSTIC-OPTICAL IMAGING SYSTEM

(71) Applicant: Commissariat à l'Energie Atomique et aux Energies Alternatives, Paris (FR)

(72) Inventors: Arnaud Verdant, Grenoble (FR); William Guicquero, Grenoble (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 97 days.

(21) Appl. No.: 16/946,240

(22) Filed: Jun. 11, 2020

(65) Prior Publication Data
US 2020/0393362 A1  Dec. 17, 2020

(30) Foreign Application Priority Data
Jun. 13, 2019  (FR) ..................... 1906281

(51) Int. Cl.
*G01N 21/17*  (2006.01)
*G01N 21/47*  (2006.01)
(Continued)

(52) U.S. Cl.
CPC ..... *G01N 21/1717* (2013.01); *G01N 21/4788* (2013.01); *G02F 1/11* (2013.01); *G02F 2/00* (2013.01); *G01N 2021/479* (2013.01)

(58) Field of Classification Search
CPC .......... G01N 21/1717; G01N 21/4788; G01N 2021/479; G01N 21/45; G01N 29/2418; G02F 1/11; G02F 2/00; A61B 5/0095
See application file for complete search history.

(56) References Cited

U.S. PATENT DOCUMENTS 5,459,432 A * 10/1995 White ............... G01C 19/5607
                                                    329/307
5,617,090 A *  4/1997 Ma ........................ H03M 3/474
                                                    341/141
(Continued)

FOREIGN PATENT DOCUMENTS

CA     3038074 C  * 11/2019  ............. G02B 5/28
GB     2113862 A  *  8/1983  ............. G02F 1/125
(Continued)

OTHER PUBLICATIONS

A. Bhandari et al., "Resolving multipath interference in time-of-flight imaging via modulation frequency diversity and sparse regularization," Optics Letters, vol. 39, No. 6, Mar. 15, 2014, pp. 1705-1708.
(Continued)

*Primary Examiner* — Mohamed K Amara
(74) *Attorney, Agent, or Firm* — Moreno IP Law LLC

(57) ABSTRACT

The present invention relates to an imaging system, including: a coherent light source delivering an object beam and a reference beam; a device of modulation of the object beam with a modulation signal; an image sensor arranged to receive an interference pattern resulting from a combination of the object beam and of the reference beam; and a demodulation device, the system being configured to, during a measurement phase: apply to the modulation signal a first pseudo-random sequence of jumps of a parameter selected among the phase, the frequency, and the amplitude; and simultaneously apply to the modulated portion of the object beam a second pseudo-random sequence of jumps of said parameter, wherein the first and second sequences of jumps of said parameter are non-correlated.

10 Claims, 4 Drawing Sheets

(51) Int. Cl.
*G02F 1/11* (2006.01)
*G02F 2/00* (2006.01)

(56) References Cited

U.S. PATENT DOCUMENTS

| | | | | |
|---|---|---|---|---|
| 5,621,345 | A * | 4/1997 | Lee | H03D 7/165 |
| | | | | 327/254 |
| 5,667,373 | A * | 9/1997 | Wright | G01S 7/52026 |
| | | | | 600/443 |
| 6,262,818 | B1 * | 7/2001 | Cuche | G03H 1/0443 |
| | | | | 359/10 |
| 6,429,797 | B1 * | 8/2002 | Wu | H03H 17/0621 |
| | | | | 341/143 |
| 7,466,255 | B1 * | 12/2008 | Ignjatovic | H01L 27/14609 |
| | | | | 341/143 |
| 8,094,058 | B2 * | 1/2012 | Jung | H03M 3/39 |
| | | | | 341/166 |
| 8,174,424 | B2 * | 5/2012 | Ignjatovic | H03M 3/434 |
| | | | | 341/164 |
| 9,958,828 | B2 * | 5/2018 | Laforest | G03H 1/0443 |
| 10,067,055 | B1 * | 9/2018 | Vakhshoori | G01J 3/4338 |
| 2005/0078316 | A1 * | 4/2005 | Ronnekleiv | G01D 5/35312 |
| | | | | 356/478 |
| 2007/0071456 | A1 * | 3/2007 | Chen | H04B 10/615 |
| | | | | 398/204 |
| 2009/0051577 | A1 * | 2/2009 | Rzehak | H03M 3/474 |
| | | | | 341/143 |
| 2016/0146662 | A1 * | 5/2016 | Stokely | G01N 29/14 |
| | | | | 73/643 |
| 2016/0191163 | A1 * | 6/2016 | Preston | H04B 10/2575 |
| | | | | 398/16 |
| 2016/0320232 | A1 * | 11/2016 | Nunes | E21B 47/095 |
| 2016/0327904 | A1 | 11/2016 | Laforest et al. | |
| 2019/0265351 | A1 * | 8/2019 | Madison | G01S 17/10 |
| 2020/0209020 | A1 * | 7/2020 | Issa | G01B 11/18 |

FOREIGN PATENT DOCUMENTS

| | | | | |
|---|---|---|---|---|
| KR | 102087623 B1 * | 3/2020 | | G01B 9/02 |
| RU | 2559869 C1 * | 8/2015 | | B61L 25/02 |
| WO | WO-2013083269 A2 * | 6/2013 | | G01S 13/003 |

OTHER PUBLICATIONS

M. Gross et al., "Detection of the tagged or untagged photons in acousto-optic imaging of thick highly scattering media by photorefractive adaptive holography," European Physics Journal E, vol. 28, 2009, pp. 173-182.

Preliminary Search Report for French Application No. FR1906281 dated Feb. 27, 2020, 2 pages.

Guillaume et al., "Acousto-optical coherence tomography with a digital holographic detection scheme," Optics Letters, vol. 37, No. 15, Aug. 1, 2012, pp. 3216-3218.

* cited by examiner

ACOUSTIC-OPTICAL IMAGING SYSTEM

FIELD

The present disclosure concerns the field of acoustic-optical imaging, particularly for medical applications.

BACKGROUND

In a biological medium such as a human or animal tissue, visible light propagates according to a diffusion regime. In such a regime, the photons follow multiple optical paths, so that their relative arrangements are modified all along the propagation of light through the medium. It is then impossible, with a standard image sensor, to acquire a faithful image of the medium crossed by the light.

To obtain information of local absorption in the medium, so-called acoustic-optical imaging techniques have already been provided, where the observed medium is illuminated by a coherent light beam, typically a laser beam, and a portion of the observed medium is submitted to an acoustic wave, typically an ultrasound acoustic wave. The vibration of the diffusers along the propagation path of the acoustic wave, also called acoustic marking area or also acoustic marking column, and then modulates the phase of the diffused photons. At the output of the medium, one can find photons carrying the acoustic modulation, called marked photons, corresponding to the photons which have crossed the acoustic marking area, and photons which do not carry the acoustic modulation, called unmarked photons, corresponding to the photons which have not crossed the acoustic marking area. An interference between the light beam originating from the medium, called object beam, and a reference beam originating from the same light source but which has not crossed the diffusing medium, is then caused. This enables to demodulate the object beam and to take the pulse of the marked photons down to the frequency of the acoustic wave. An image sensor is then used to measure the optical signal modulated at the acoustic frequency and to deduce therefrom information relative to the absorption of light in the marking area.

It would be desirable to have an acoustic-optical imaging system, this system overcoming all or part of the disadvantages of known acoustic-optical imaging systems.

SUMMARY

For this purpose, an embodiment provides an imaging system, comprising:

a coherent light source delivering an object beam and a reference beam;

a modulation device capable of modulating all or part of the object beam with a modulation signal;

an image sensor arranged to receive an interference pattern resulting from a combination of the object beam and of the reference beam; and a device for demodulating the modulated portion of the object beam, the system being configured to, during a measurement phase:

apply to the modulation signal, via the modulation device, a first pseudo-random sequence of jumps of a parameter selected among the phase, the frequency, and the amplitude; and simultaneously apply to the modulated portion of the object beam, via the demodulation device, a second pseudo-random sequence of jumps of said parameter, wherein the first and second sequences of jumps of said parameter are non-correlated.

According to an embodiment, the system is configured to, during an acquisition phase, implement M successive measurement phases, M being an integer greater than or equal to 2, and, at each measurement phase, acquire, via the image sensor, a value representative of the complex field of the modulated portion of the object beam.

According to an embodiment, the system comprises a processing device configured to implement a step of reconstruction, based on the M values acquired during the acquisition phase, of a set of L values representative of the light absorption at L different positions on the optical path of the modulated portion of the object beam, L being an integer greater than or equal to 2.

According to an embodiment, L is greater than M.

According to an embodiment, the modulation device is an acoustic-optical modulation device.

According to an embodiment, the modulation device comprises an ultrasound transducer, the modulation signal being an ultrasound wave applied by the ultrasound transducer to a portion of a sample to be analyzed, placed on the optical path of the object beam.

According to an embodiment, the modulation device comprises a plurality of ultrasound transducers arranged in an array, linear or not, and, during each measurement phase, the ultrasound modulation wave is emitted in fractions by the different transducers according to a pseudo-random function γ.

According to an embodiment, the modulation device comprises an acoustic-optical modulator placed on the optical path of the object beam upstream of a scene to be analyzed.

According to an embodiment, the demodulation device is an electronic demodulation device integrated to the image sensor.

According to an embodiment, the demodulation device comprises an acoustic-optical modulator placed on the optical path of the reference beam, upstream of the image sensor.

BRIEF DESCRIPTION OF THE DRAWINGS

The foregoing features and advantages, as well as others, will be described in detail in the following description of specific embodiments given by way of illustration and not limitation with reference to the accompanying drawings, in which.

DETAILED DESCRIPTION OF THE PRESENT EMBODIMENTS

Like features have been designated by like references in the various figures. In particular, the structural and/or functional features that are common among the various embodiments may have the same references and may dispose identical structural, dimensional and material properties.

For the sake of clarity, only the steps and elements that are useful for an understanding of the embodiments described herein have been illustrated and described in detail. In particular, the imaging applications capable of being implemented based on the described sensors have not been detailed, the described embodiments being compatible with usual acoustic-optical imaging applications in the medical field or in other fields.

Unless indicated otherwise, when reference is made to two elements connected together, this signifies a direct connection without any intermediate elements other than conductors, and when reference is made to two elements coupled together, this signifies that these two elements can be connected or they can be coupled via one or more other elements.

In the following description, when reference is made to terms qualifying absolute positions, such as terms "front", "rear", "top", "bottom", "left", "right", etc., or relative positions, such as terms "above", "under", "upper", "lower", etc., or to terms qualifying directions, such as terms "horizontal", "vertical", etc., unless otherwise specified, it is referred to the orientation of the drawings, it being understood that, in practice, the described devices may be oriented differently.

Unless specified otherwise, the expressions "around", "approximately", "substantially" and "in the order of" signify within 10%, and preferably within 5%.

Figure 1:
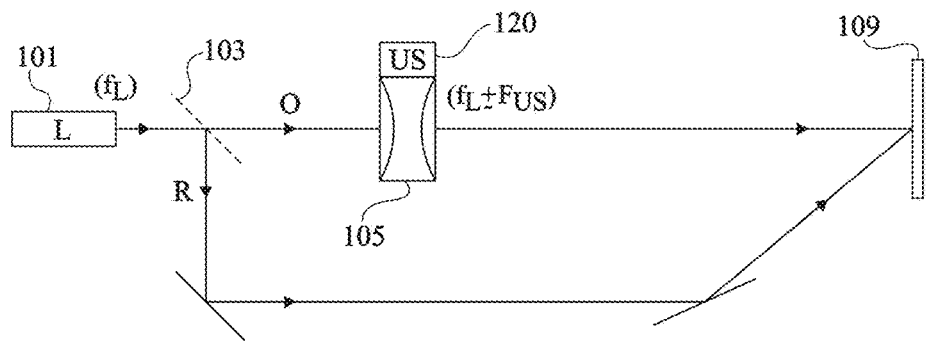
FIG. 1 schematically shows an example of an acoustic-optical imaging system.

FIG. 1 schematically shows an example of an acoustic-optical imaging system.

The system of FIG. 1 comprises a light source 101 (L) capable of generating a coherent light beam of frequency $f_L$, for example, a laser source. The system further comprises a splitter 103, for example, a beam splitter 103 placed with a 45-degree angle with respect to the emission direction of source 101, enabling to divide the beam generated by source 101 into an object beam O and a reference beam R. The system is arranged so that object beam O illuminates an object or a sample 105 to be analyzed, and so that reference beam R does not cross object 105. The reference beam and the object beam reflected or transmitted by object 105 are then projected onto an image sensor 109 comprising an array of pixels (not detailed), to generate an interference pattern in the acquisition plane of the sensor.

In the system of FIG. 1, a portion of the object or sample 105 is excited by a sine acoustic wave of frequency $F_{US}$, for example in the range from 1 to 15 MHz, for example generated by an ultrasound transducer 120. As a result, the frequency of the rays of the object beam crossing the excited portion of the sample is shifted to value $f_L + F_{US}$ or $f_L - F_{US}$, while the frequency of the rays of the object beam crossing the non-excited portion of the sample remains at value $f_L$. Such a frequency shift enables to "mark" the photons of the object beam having crossed the excited portion of the sample, called marking area, with respect to the other photons of the object beam. It is then desired to measure the energy carried by the marked photons, to deduce therefrom information relative to light absorption in the marking area.

Figure 2:
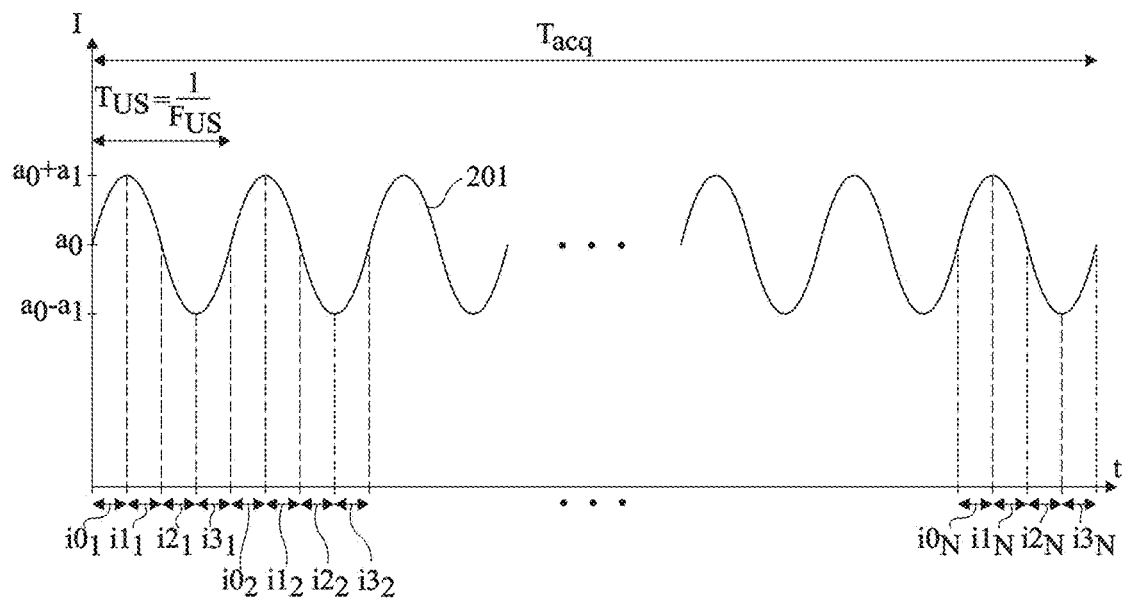
FIG. 2 is a diagram illustrating the operation of the circuit of FIG. 1.

FIG. 2 is a diagram illustrating in further detail the operation of the system of FIG. 1.

The diagram of FIG. 2 comprises a curve 201 showing the variation over time t (in abscissas) of the light intensity I (in ordinates) received by a pixel of sensor 109 of the system of FIG. 1, when sensor 109 is illuminated by the combination of the object beam and of the reference beam.

In operation, sensor 109 sees an interference pattern also called speckle pattern, formed of speckles resulting from the constructive or destructive interferences of the diffuse object beam. Each speckle has a relatively constant modulus over the total extent of the speckle, first depending on the photon absorption in the marking area, and a random phase depending on the optical paths followed by light in the medium. The spatial sampling of the speckles is preferably such that each speckle covers at least one pixel. The interference with the reference beam results in the creation of interference fringes. The angle of incidence of the reference beam on the sensor may be controlled to obtain the desired spatial period between fringes. The interference pattern seen by sensor 109 has a beat frequency equal to acoustic modulation frequency $F_{US}$. Thus, as shown in FIG. 2, the intensity I received by each pixel varies in sinusoidal fashion around an average value or DC component $a_0$, with a peak amplitude of value $a_1$, at a frequency equal to the acoustic modulation frequency $F_{US}$ of the system. The light intensities received by different pixels of sensor 109 may have different DC components $a_0$ and/or different amplitudes $a_1$, but all fluctuate in sinusoidal fashion at beat frequency $F_{US}$, with specific phase shifts.

Each pixel of sensor 109 comprises a photodiode (not shown) supplying a current representative of the light intensity received by the pixel.

In this example, the measurement of the marked portion of the object beam is performed during an acquisition period $T_{acq}$ of duration $N*T_{US}$, where $T_{US}$ designates the period of acoustic modulation of the system, equal to $1/F_{US}$, and where N is an integer, greater than or equal to 1, for example, in the range from 100 to 10,000.

Each pixel comprises an integration circuit configured to, at each period of acoustic modulation $T_{US}$ of acquisition period $T_{acq}$, integrate the photocurrent delivered by the photodiode successively in K=4 different capacitors C0, C1, C2, and C3 (not shown). Such a four-phase integration and sampling cycle is successively repeated N times during period $T_{acq}$, it being understood that the integration capacitors C0, C1, C2, and C3 of the pixel are not reset between the beginning and the end of period $T_{acq}$. The accumulation of the samples over a high number N of periods of the acoustic modulation signal enables to improve the signal-to-noise ratio of the measurement. Number N is preferably selected so that the duration of acquisition phase $T_{acq}$ remains shorter than a characteristic duration of decorrelation of the medium, for example, in the range from 0.1 to 5 ms, for example, in the order of 1 ms, corresponding to the time beyond which the amplitude and the phase of the measured signal risk varying due to physiological variations of the observed medium (for example, due to a blood platelet movement).

In FIG. 2, for each of the N periods $T_{US}$ of acquisition phase $T_{acq}$, references $i0_p$, $i1_p$, $i2_p$, and $i3_p$, designate the four successive periods of integration of the photocurrent delivered by the pixel photodiode, respectively in the four capacitors C0, C1, C2, and C3 of the pixel, where p is an integer in the range from 1 to N designating the rank of the acoustic modulation period $T_{US}$ considered in acquisition phase $T_{acq}$. In this example, integration periods $i0_p$, $i1_p$, $i2_p$, and $i3_p$ all substantially have the same duration, in the order of $T_{US}/4$.

At the end of acquisition phase $T_{acq}$, each pixel of the sensor delivers four values I0, I1, I2, and I3 respectively representative of the voltages across capacitors C0, C1, C2, and C3 of the pixel.

Based on these four values, the complex field $E_{OM}$ of the portion of the object beam marked by the acoustic modulation may be determined, for each pixel of the sensor, by formula $E_{OM}=(I0-I2)+i(I1-I3)$, i being the imaginary unit. Component I0-I2 corresponds to the real part of field $E_{OM}$, and component I1-I3 corresponds to the imaginary part of field $E_{OM}$. The phase $P_{OM}$ and the amplitude $A_{OM}$ of the marked object beam received by each pixel of the sensor may be determined by the following formulas:

$$P_{OM} = \arctan\left(\frac{I1-I3}{I0-I2}\right) \quad [\text{Eq. 1}]$$

and $$A_{OM} = \sqrt{(I0-I2)^2+(I1-I3)^2} \quad [\text{Eq. 2}]$$

Knowing the amplitude $A_{OM}$ of the marked object beam enables, in particular, to obtain information relative to light absorption in the acoustic marking area, for example, to detect the possible presence of an absorbing body, for example, a tumor, in the marking area.

It should be noted that the acquisition technique described in relation with FIGS. 1 and 2 only enables to determine the average absorption within the marking area, but does not provide information relative to the absorption in local regions of the marking area.

Figure 3:
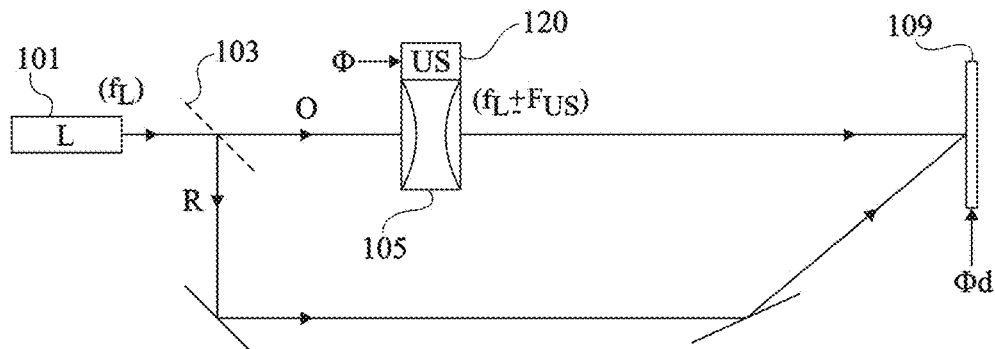
FIG. 3 schematically shows another example of an acoustic-optical imaging system.

FIG. 3 schematically shows another example of an acoustic-optical imaging system, enabling to determine the absorption in local regions of the marking area.

The system of FIG. 3 differs from the system of FIG. 1 mainly in that, in the system of FIG. 3, a sequence Φ of phase jumps with a random or pseudo-random pattern, called modulation sequence, is applied to the acoustic marking wave. As an example, at each new acoustic modulation period $T_{US}$, a phase jump of value 0 or π, randomly or pseudo-randomly selected, is applied to the acoustic marking wave. At the level of sensor 109, after the interference of the object beam with the reference beam, the signal is sampled according to the four-phase demodulation method discussed in relation with FIG. 2, adapted to take into account the sequence Φ of phase jumps applied to the acoustic marking wave.

Figure 4:
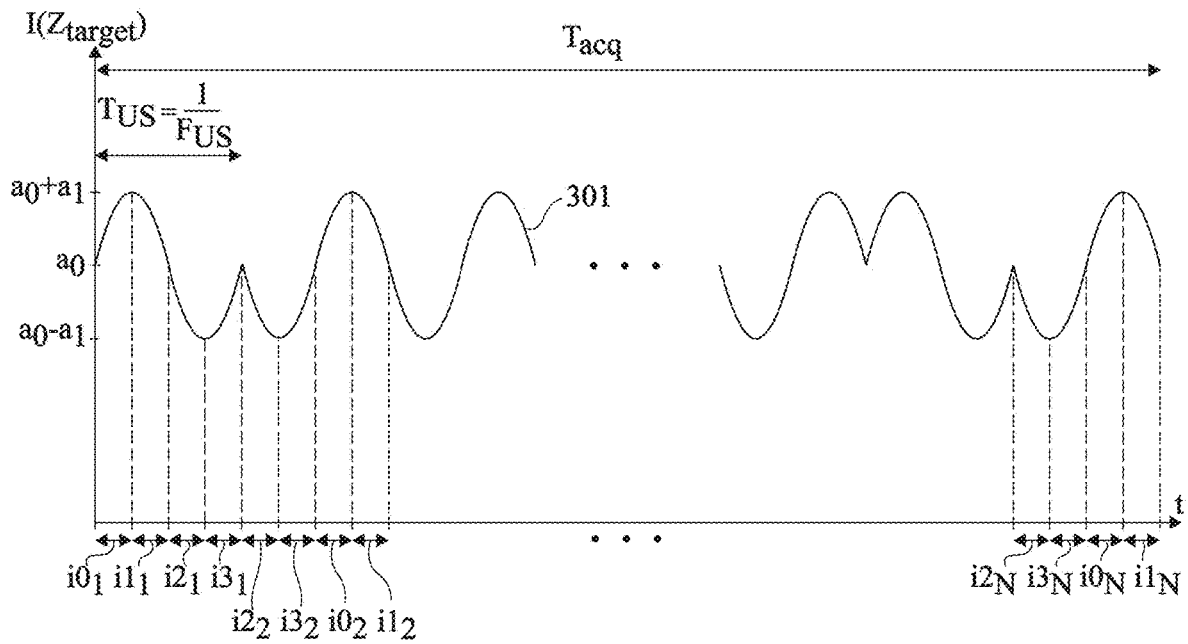
FIG. 4 is a diagram illustrating the operation of the circuit of FIG. 3.

FIG. 4 is a diagram illustrating in further detail the operation of the system of FIG. 3.

The diagram of FIG. 4 comprises a curve 301 representing the variation, over time t, in abscissas, of the contribution $I(Z_{target})$, in ordinates, of a local position $Z_{target}$ of the marking area, to the object optical signal received by sensor 109 after the interference with the reference signal. In this example, position $Z_{target}$ corresponds to a position in the propagation axis of the acoustic modulation wave.

Intensity $I(Z_{target})$ varies in sinusoidal fashion around an average value or DC component $a_0$, with a peak amplitude of value $a_1$, at a frequency equal to the acoustic modulation frequency $F_{US}$ of the system. In this example, at each new period $T_{US}$ of acquisition phase $T_{acq}$, intensity $I(Z_{target})$ is submitted to a 0 or π phase jump. The sequence Φd of phase jumps applied to intensity $I(Z_{target})$ corresponds to the sequence (of phase jumps applied to the acoustic marking wave, delayed by a delay $\Delta t=Z_{target}/\upsilon_{US}$, $\upsilon_{US}$ designating the propagation speed of the acoustic marking wave in the observed medium.

In each pixel of the sensor, the integration circuit is configured to, at each acoustic modulation period $T_{US}$ of acquisition period $T_{acq}$, integrate the photocurrent delivered by the photodiode successively in the four capacitors C0, C1, C2, and C3 (not shown), taking into account the delayed phase jump pattern $\Phi d=\Phi(t-\Delta t)$, called modulation sequence, to determine the order in which capacitors C0, C1, C2, and C3 are connected to the photodiode. More particularly, in this example, at each phase jump of value π in sequence Φd, the order of integration of the photocurrent in capacitors C0 and C2 on the one hand and C1 and C3 on the other hand is inverted.

At the end of acquisition phase $T_{acq}$, each pixel of the sensor delivers four values I0, I1, I2, and I3 respectively representative of the voltages across capacitors C0, C1, C2, and C3 of the pixel. Values I0, I1, I2, and I3 are mainly representative of the contribution to the object optical signal received by the pixel, of the position of the marking area for which phase jump pattern Φd is correlated to the acoustic modulation signal, that is, position $Z_{target}=\upsilon_{US}*\Delta t$.

Based on these four values, the complex field $E_{OM}$ of the portion of the object beam marked by the acoustic modulation at position $Z_{target}$ of the marking area may be determined by formula $E_{OM}=(I0-I2)+j(I1-I3)$. Component I0-I2 corresponds to the real part of field $E_{OM}$, and component I1-I3 corresponds to the imaginary part of field $E_{OM}$. The phase $P_{OM}$ and the amplitude $A_{OM}$ of the marked object beam received from position $Z_{target}$ may be determined by the same formulas 1 and 2 as in the example of FIGS. 1 and 2.

The measurement may be repeated by modifying the delay Δt between the phase jump sequence Φ applied to the acoustic modulation signal and the sequence Φd applied to the sensor during acquisition phase $T_{acq}$, to measure the field $E_{OM}$ originating from another target position $Z_{target}$ in the marking area. More particularly, calling L the desired axial resolution, that is, the desired number of measurement points having different positions $Z_{target}$ in the acoustic marking target (that is, along the main propagation axis of the acoustic marking beam), the measurement should be repeated L times.

Figure 5:
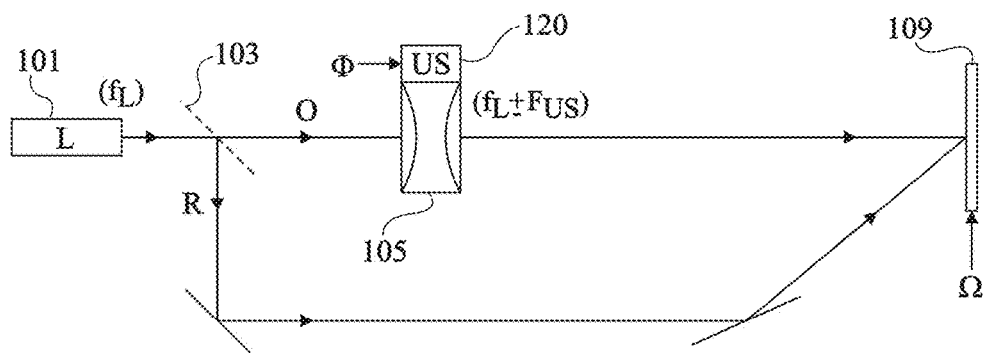
FIG. 5 schematically shows an example of an acoustic-optical imaging system according to a first embodiment.

FIG. 5 schematically shows an example of an acoustic-optical imaging system according to a first embodiment.

The system of FIG. 5 comprises the same elements as the system of FIG. 3, arranged substantially in the same way, and differs from the system of FIG. 3 mainly by its operating mode.

In the embodiment of FIG. 5, it is provided to reconstruct an absorption profile of the marking column, of axial resolution L, based on a series of M measurements, L and M being integers greater than or equal to 2. During each measurement, a first random or pseudo-random phase jump sequence Φ, called modulation sequence, is applied to the acoustic marking signal, identically or similarly to what has been described in the example of FIGS. 3 and 4. During acquisition phase $T_{acq}$, each pixel of sensor 109 applies to the measured signal a second random or pseudo-random phase jump sequence Ω, called demodulation sequence. As an example, at each new acoustic modulation period $T_{US}$ of acquisition phase $T_{acq}$, a phase jump of value 0 or π is applied to the measured signal. The N phase jump values applied during acquisition phase $T_{acq}$ define sequence Ω. In each pixel of sensor, the integration circuit is configured to, at each acoustic modulation period $T_{US}$ of acquisition phase $T_{acq}$, integrate the photocurrent delivered by the photodiode successively in the four capacitors C0, C1, C2, and C3, taking into account sequence Ω to determine the order in which capacitors C0, C1, C2, and C3 are connected to the photodiode. More particularly, in this example, at each phase jump of value π in sequence Ω, the order of integration of the photocurrent in capacitors C0 and C2 on the one hand and C1 and C3 on the other hand is inverted.

Conversely to the example of FIGS. 3 and 4 where the modulation sequence Φ of the phase of the acoustic marking beam and the demodulation sequence Φd controlling the sampling phases applied by sensor 109 during acquisition phase $T_{acq}$ have a correlation peak defined for a specific position in the marking column, in the example of FIG. 5, the modulation and demodulation sequences Φ and Ω are non-correlated. Sequences Φ and Ω for example correspond to two independent random or pseudo-random drawings of binary sequences, for example, random drawings according to an equiprobable Bernoulli distribution, where a state of the binary sequence corresponds to a modulation period $T_{US}$. Two new random or pseudo-random drawings independent from the previous drawing, that is, non-correlated with the previous drawing, may be applied to each of the M measurements of the phase of acquisition of the absorption profile of the sample (that is, 2*M distinct drawings which are not correlated together for the acquisition of an absorption profile of L values). Each measurement then results from a variable contribution of the different points of the marking column of the sample.

The inventors have shown that an acquisition model may be constructed, enabling to model the measurements as a projection of the desired absorption profile through a transition matrix.

The light signal s(t) seen at the level of a pixel of sensor 109, resulting from the interference between the object beam (signal $E_s(t)$) and the reference beam (signal $E_r(t)$) is provided by the following equation:

$$s(t) = |E_r(t) + E_s(t)|^2 \quad \text{[Eq. 3]}$$

with:

$$E_r(t) = A_R e^{i\omega_L t} \quad \text{[Eq. 4]}$$

and:

$$E_s(t) = A_D e^{i\omega_L t} + \int_z a_M(z) e^{i(\omega_L t + \omega_{US}(t - z/v_{US}) + \pi\Phi(t - z/v_{US} + \delta))} dz + \int_z a_M(z) e^{i(\omega_L t - \omega_{US}(t - z/v_{US}) - \pi\Phi(t - z/v_{US} + \delta))} dz \quad \text{[Eq. 5]}$$

where $A_R$, $A_D$, and $a_M$ are the complex amplitudes of the optical fields respectively of the reference arm, unmarked photons of the object arm, and marked photons of the object arm, t is a time variable, z designates the position along the acoustic marking column of sample ($a_M(z)$ corresponds to the absorption of the sample at position z of the marking column), $v_{US}$ designates the propagation speed of the acoustic wave in the sample, $\omega_L$ and $\omega_{US}$ respectively designate the pulse of the light wave emitted by source 101 and the pulse of the acoustic marking wave, Φ designates the binary sequence of modulation of the phase of the acoustic marking wave, and δ is a term reflecting the fact that the phase of the modulating signal may be non-zero at the origin.

Signal s(t) may then be expressed as follows:

$$s(t) = \left( |e^{i\omega_L t}| \cdot \left| A_D + A_R + \int_z a_M(z) e^{i(\omega_{US}(t - z/v_{US}) + \pi\Phi(t - z/v_{US} + \delta))} dz + \int_M a_M(z) e^{-i(\omega_{US}(t - z/v_{US}) - \pi\Phi(t - z/v_{US} + \delta))} dz \right| \right)^2 \quad \text{[Eq. 6]}$$

and then:

$$s(t) = |A_D + A_R + 2\int_z a_M(z)\cos(\omega_{US}(t - z/v_{US}) + \pi\Phi(t - z/v_{US} + \delta))dz|^2 \quad \text{[Eq. 7]}$$

For each of the M measurements of the phase of acquisition of the absorption profile, a term I=I0–I2 and a term Q=I1–I3 is measured at the sensor level, by the above-discussed four-phase demodulation technique, with:

$$I = \sum_{p=1}^{N} \Pi(p) \left( \int_{pT_{US}}^{pT_{US}+T_{US}/4} s(t)dt - \int_{pT_{US}+T_{US}/2}^{pT_{US}+3T_{US}/4} s(t)dt \right) \quad \text{[Eq. 8]}$$

and:

$$Q = \sum_{p=1}^{N} \Pi(p) \left( \int_{pT_{US}+T_{US}/4}^{pT_{US}+T_{US}/2} s(t)dt - \int_{pT_{US}+3T_{US}/4}^{pT_{US}+T_{US}} s(t)dt \right) \quad \text{[Eq. 9]}$$

with:

$$\Pi(p) = 2\left(\Omega(P) - \frac{1}{2}\right) \quad \text{[Eq. 10]}$$

where Ω designates the binary demodulation sequence applied by sensor 109.

Term Q can be expressed as follows:

$$Q = \sum_{p=1}^{N} \Pi(p) \quad \text{[Eq. 11]}$$

$$\left( \int_{pT_{US}+T_{US}/4}^{pT_{US}+T_{US}/2} \left( \text{Re}\left( \begin{array}{c} A_D + A_R + 2\int_z a_M(z)\cos \\ (\omega_{US}(t - z/v_{US}) + \pi\Phi(t - z/v_{US} + \delta))dz \end{array} \right) \right)^2 dt - \right.$$

$$\int_{pT_{US}+3T_{US}/4}^{pT_{US}+T_{US}} \left( \text{Re}\left( \begin{array}{c} A_D + A_R + 2\int_z a_M(z)\cos \\ (\omega_{US}(t - z/v_{US}) + \pi\Phi(t - z/v_{US} + \delta))dz \end{array} \right) \right)^2 dt +$$

$$\int_{pT_{US}+T_{US}/4}^{pT_{US}+T_{US}/2} \left( \text{Im}\left( \begin{array}{c} A_D + A_R + 2\int_z a_M(z)\cos \\ (\omega_{US}(t - z/v_{US}) + \pi\Phi(t - z/v_{US} + \delta))dz \end{array} \right) \right)^2 dt -$$

$$\left. \int_{pT_{US}+3T_{US}/4}^{pT_{US}+T_{US}} \left( \text{Im}\left( \begin{array}{c} A_D + A_R + 2\int_z a_M(z)\cos \\ (\omega_{US}(t - z/v_{US}) + \pi\Phi(t - z/v_{US} + \delta))dz \end{array} \right) \right)^2 dt \right)$$

where Re and Im respectively designate the real part and the imaginary part of a complex number.

The terms which do not comprise the component $A_R$ of the reference arm may be neglected, the energy provided by this arm being much greater than the energy provided by the marked and unmarked portions of the object arm.

Equation 11 can then be simplified as follows:

[Eq. 12]

$$Q = \sum_{p=1}^{N} \Pi(p) \left\{ \begin{array}{l} \int_{pT_{US}+T_{US}/4}^{pT_{US}+T_{US}/2} 4\text{Re}(A_R)\left(\int_z \text{Re}(a_M(z)G(t, z))dz\right)dt - \\ \int_{pT_{US}+3T_{US}/4}^{pT_{US}+T_{US}} 4\text{Re}(A_R)\left(\int_z \text{Re}(a_M(z)G(t, z))dz\right)dt + \\ \int_{pT_{US}+T_{US}/4}^{pT_{US}+T_{US}/2} 4\text{Im}(A_R)\left(\int_z \text{Im}(a_M(z)G(t, z))dz\right)dt - \\ \int_{pT_{US}+3T_{US}/4}^{pT_{US}+T_{US}} 4\text{Im}(A_R)\left(\int_z \text{Im}(a_M(z)G(t, z))dz\right)dt \end{array} \right\} \quad \text{with:}$$

$$G(t, z) = \cos(\omega_{US}(t - z/v_{US}) + \pi\Phi(t - z/v_{US} + \delta)) \quad \text{[Eq. 13]}$$

Similarly, term I may be expressed as follows:

$$I = \sum_{p=1}^{N} \Pi(p) \begin{cases} \int_{pT_{US}}^{pT_{US}+T_{US}/2} 4\text{Re}(A_R)\left(\int_z \text{Re}(a_M(z)G(t,z))dz\right)dt - \\ \int_{pT_{US}+T_{US}/2}^{pT_{US}+3T_{US}/4} 4\text{Re}(A_R)\left(\int_z \text{Re}(a_M(z)G(t,z))dz\right)dt + \\ \int_{pT_{US}}^{pT_{US}+T_{US}/4} 4\text{Im}(A_R)\left(\int_z \text{Im}(a_M(z)G(t,z))dz\right)dt - \\ \int_{pT_{US}+T_{US}/2}^{pT_{US}+3T_{US}/4} 4\text{Im}(A_R)\left(\int_z \text{Im}(a_M(z)G(t,z))dz\right)dt \end{cases}$$ [Eq. 14]

Terms Q and I may be re-expressed as follows:

$$Q = \sum_{p=1}^{N} \Pi(p) \begin{cases} \int_{pT_{US}+T_{US}/4}^{pT_{US}+T_{US}/2} 4\text{Re}(A_R)\left(\int_z (\text{Re}(a_M(z))\text{Re}(G(t,z)) - \text{Im}(a_M(z))\text{Im}(G(t,z)))dz\right)dt - \\ \int_{pT_{US}+3T_{US}/4}^{pT_{US}+T_{US}} 4\text{Re}(A_R)\left(\int_z (\text{Re}(a_M(z))\text{Re}(G(t,z)) - \text{Im}(a_M(z))\text{Im}(G(t,z)))dz\right)dt + \\ \int_{pT_{US}+T_{US}/4}^{pT_{US}+T_{US}/2} 4\text{Im}(A_R)\left(\int_z (\text{Re}(a_M(z))\text{Im}(G(t,z)) + \text{Im}(a_M(z))\text{Re}(G(t,z)))dz\right)dt - \\ \int_{pT_{US}+3T_{US}/4}^{pT_{US}+T_{US}} 4\text{Im}(A_R)\left(\int_z (\text{Re}(a_M(z))\text{Im}(G(t,z)) + \text{Im}(a_M(z))\text{Re}(G(t,z)))dz\right)dt \end{cases}$$ [Eq. 15]

and:

$$I = \sum_{p=1}^{N} \Pi(p) \begin{cases} \int_{pT_{US}}^{pT_{US}+T_{US}/4} 4\text{Re}(A_R)\left(\int_z (\text{Re}(a_M(z))\text{Re}(G(t,z)) - \text{Im}(a_M(z))\text{Im}(G(t,z)))dz\right)dt - \\ \int_{pT_{US}+T_{US}/2}^{pT_{US}+3T_{US}/4} 4\text{Re}(A_R)\left(\int_z (\text{Re}(a_M(z))\text{Re}(G(t,z)) - \text{Im}(a_M(z))\text{Im}(G(t,z)))dz\right)dt + \\ \int_{pT_{US}}^{pT_{US}+T_{US}/4} 4\text{Im}(A_R)\left(\int_z (\text{Re}(a_M(z))\text{Im}(G(t,z)) + \text{Im}(a_M(z))\text{Re}(G(t,z)))dz\right)dt - \\ \int_{pT_{US}+T_{US}/2}^{pT_{US}+3T_{US}/4} 4\text{Im}(A_R)\left(\int_z (\text{Re}(a_M(z))\text{Im}(G(t,z)) + \text{Im}(a_M(z))\text{Re}(G(t,z)))dz\right)dt \end{cases}$$ [Eq. 16]

that is:

$$Q = \int_z \text{Re}(a_M(z))\left(4\text{Re}(A_R)\left(\sum_{p=1}^{N} \Pi(p)\right)\left(\int_{pT_{US}+T_{US}/4}^{pT_{US}+T_{US}/2} \text{Re}(G(t,z))dt - \int_{pT_{US}+3T_{US}/4}^{pT_{US}+T_{US}} \text{Re}(G(t,z))dt\right)\right) +$$

$$4\text{Im}(A_R)\left(\sum_{p=1}^{N} \Pi(p)\left(\int_{pT_{US}+T_{US}/4}^{pT_{US}+T_{US}/2} \text{Im}(G(t,z))dt - \int_{pT_{US}+3T_{US}/4}^{pT_{US}+T_{US}} \text{Im}(G(t,z))dt\right)\right)dz -$$

$$\int_z \text{Im}(a_M(z))\left(4\text{Re}(A_R)\left(\sum_{p=1}^{N} \Pi(p)\left(\int_{pT_{US}+T_{US}/4}^{pT_{US}+T_{US}/2} \text{Im}(G(t,z))dt - \int_{pT_{US}+3T_{US}/4}^{pT_{US}+T_{US}} \text{Im}(G(t,z))dt\right)\right) - 4\text{Im}(A_R)\left(\sum_{p=1}^{N} \Pi(p)\right.\right.$$

$$\left.\left.\left(\int_{pT_{US}+T_{US}/4}^{pT_{US}+T_{US}/2} \text{Re}(G(t,z))dt - \int_{pT_{US}+3T_{US}/4}^{pT_{US}+T_{US}} \text{Re}(G(t,z))dt\right)\right)\right)dz$$ [Eq. 17]

$$I = \int_z \text{Re}(a_M(z))\left(4\text{Re}(A_R)\left(\sum_{p=1}^{N} \Pi(p)\right)\right.$$

$$\left.\left(\int_{pT_{US}}^{pT_{US}+T_{US}/4} \text{Re}(G(t,z))dt - \int_{pT_{US}+T_{US}/2}^{pT_{US}+3T_{US}/4} \text{Re}(G(t,z))dt\right)\right) +$$

$$4\text{Im}(A_R)\left(\sum_{p=1}^{N} \Pi(p)\left(\int_{pT_{US}}^{pT_{US}+T_{US}/4} \text{Im}(G(t,z))dt - \int_{pT_{US}+T_{US}/2}^{pT_{US}+3T_{US}/4} \text{Im}(G(t,z))dt\right)\right)dz -$$

$$\int_z \text{Im}(a_M(z))\left(4\text{Re}(A_R)\left(\sum_{p=1}^{N} \Pi(p)\left(\int_{pT_{US}}^{pT_{US}+T_{US}/4} \text{Im}(G(t,z))dt - \int_{pT_{US}+T_{US}/2}^{pT_{US}+3T_{US}/4} \text{Im}(G(t,z))dt\right)\right) - 4\text{Im}(A_R)\left(\sum_{p=1}^{N} \Pi(p)\right.\right.$$

$$\left.\left.\left(\int_{pT_{US}}^{pT_{US}+T_{US}/4} \text{Re}(G(t,z))dt - \int_{pT_{US}+T_{US}/2}^{pT_{US}+3T_{US}/4} \text{Re}(G(t,z))dt\right)\right)\right)dz$$ [Eq. 18]

Calling $Q_j$, respectively $I_j$, the term Q, respectively I, measured by the pixel at each of the M measurements of the phase of acquisition of the absorption profile, and assigning an index j to all the terms varying from one measurement to the other, j being an integer in the range from 1 to M, the equations may be rewritten, for each measurement, as follows:

$$Q_j = \int_z \text{Re}(a_M(z))C_j(z)dz - \int_z \text{Im}(a_M(z))D_j(z)dz$$ [Eq. 19]

and:

$$I_j = \int_z \text{Re}(a_M(z))E_j(z)dz - \int_z \text{Im}(a_M(z))F_j(z)dz$$ [Eq. 20]

with, knowing that $\text{Im}(G(t,z)) = 0$:

$$C_j(z) = 4\text{Re}(A_R)\sum_{p=1}^{N} \Pi_j(p)$$ [Eq. 21]

$$\left(\int_{pT_{US}+T_{US}/4}^{pT_{US}+T_{US}/2} \cos(\omega_{US}(t - z/\upsilon_{US}) + \pi\Phi_j(t - z/\upsilon_{US} + \delta_j))dt - \right.$$

$$\left.\int_{pT_{US}+3T_{US}/4}^{pT_{US}+T_{US}} \cos(\omega_{US}(t - z/\upsilon_{US}) + \pi\Phi_j(t - z/\upsilon_{US} + \delta_j))dt\right)$$

$$D_j(z) = -4\text{Im}(A_R)$$ [Eq. 22]

$$\left(\sum_{p=1}^{N}\Pi_j(p)\left(\int_{pT_{US}+T_{US}/4}^{pT_{US}+T_{US}/2}\cos(\omega_{US}(t-z/\upsilon_{US})+\pi\Phi_j(t-z/\upsilon_{US}+\delta_j))\right.\right.$$

$$\left.\left.dt-\int_{pT_{US}+3T_{US}/4}^{pT_{US}+T_{US}}\cos(\omega_{US}(t-z/\upsilon_{US})+\pi\Phi_j(t-z/\upsilon_{US}+\delta_j))dt\right)\right)$$
[Eq. 23]

$$E_j(z) = 4\mathrm{Re}(A_R)$$

$$\left(\sum_{p=1}^{N}\Pi_j(p)\left(\int_{pT_{US}}^{pT_{US}+T_{US}/4}\cos\left(\omega_{US}(t-z/\upsilon_{US})+\pi\Phi_j(t-z/\upsilon_{US}+\delta_j)\right)\right.\right.$$

$$\left.\left.dt-\int_{pT_{US}+T_{US}/2}^{pT_{US}+3T_{US}/4}\cos(\omega_{US}(t-z/\upsilon_{US})+\pi\Phi_j(t-z/\upsilon_{US}+\delta_j))dt\right)\right)$$
[Eq. 24]

$$F_j(z) = -4\mathrm{Im}(A_R)$$

$$\left(\sum_{p=1}^{N}\Pi_j(p)\left(\int_{pT_{US}}^{pT_{US}+T_{US}/4}\cos\left(\omega_{US}(t-z/\upsilon_{US})+\pi\Phi_j(t-z/\upsilon_{US}+\delta_j)\right)\right.\right.$$

$$\left.\left.dt-\int_{pT_{US}+T_{US}/2}^{pT_{US}+3T_{US}/4}\cos(\omega_{US}(t-z/\upsilon_{US})+\pi\Phi_j(t-z/\upsilon_{US}+\delta_j))dt\right)\right)$$

All the obtained measurements may be written in the form of a vector Y of M imaginary numbers Yj, with Yj=Ij+iQj, and:

$$Q_j = \sum_{k=1}^{L}\left(\mathrm{Re}(a_M(k\cdot\Delta z))\int_{(k-1)\cdot\Delta z}^{k\cdot\Delta z}C_j(z)dz - \mathrm{Im}(a_M(k\cdot\Delta z))\int_{(k-1)\cdot\Delta z}^{k\cdot\Delta z}D_j(z)dz\right)$$
[Eq. 25]

$$I_j = \sum_{k=1}^{L}\left(\mathrm{Re}(a_M(k\cdot\Delta z))\int_{(k-1)\cdot\Delta z}^{k\cdot\Delta z}E_j(z)dz - \mathrm{Im}(a_M(k\cdot\Delta z))\int_{(k-1)\cdot\Delta z}^{k\cdot\Delta z}F_j(z)dz\right)$$
[Eq. 26]

where $\Delta z$ represents a fraction of the wavelength $\lambda_{US}=T_{US}*\upsilon_{US}$ of the acoustic pulse signal $\omega_{US}$, defining the desired axial measurement resolution (L*$\Delta z$ corresponding to the thickness of the analyzed medium, that is, the length of the marking column having its absorption profile desired to be acquired). The absorption of the medium in a section of length $\Delta z$ of the marking column is considered as constant along the section length $\Delta z$.

In this example, to construct the transition matrix of the system, terms I and Q are rewritten by considering, for each position z along the marking column, a predetermined reference contribution $a_{Mref}(z)$ to the marked portion of the object beam received by the sensor, enabling for example to model the acoustic marking efficiency along the column (for example to take into account a possible lack of uniformity of the acoustic power density along the column). Term $a_{Mref}$ is a predetermined vector of L values, defined according to the properties of the imaging system, and particularly to the properties of the transducer used to generate the acoustic marking wave. On can then write, for each of the M measurements:

$$Q_{jRef} = \sum_{k=1}^{L}\left(\mathrm{Re}(a_{MRef}(k\cdot\Delta z))\int_{(k-1)\cdot\Delta z}^{k\cdot\Delta z}C_j(z)dz - \right.$$
[Eq. 27]

$$\left.\mathrm{Im}(a_{MRef}(k\cdot\Delta z))\int_{(k-1)\cdot\Delta z}^{k\cdot\Delta z}D_j(z)dz\right) \text{ and:}$$

$$I_{jRef} = \sum_{k=1}^{L}\left(\mathrm{Re}(a_{MRef}(k\cdot\Delta z))\int_{(k-1)\cdot\Delta z}^{k\cdot\Delta z}E_j(z)dz - \right.$$
[Eq. 28]

$$\left.\mathrm{Im}(a_{MRef}(k\cdot\Delta z))\int_{(k-1)\cdot\Delta z}^{k\cdot\Delta z}F_j(z)dz\right)$$

and then:

$$Y_{jRef} = \sum_{k=1}^{L}\left(\mathrm{Re}(a_{MRef}(k\cdot\Delta z))\int_{(k-1)\cdot\Delta z}^{k\cdot\Delta z}E_j(z)dz - \right.$$
[Eq. 29]

$$\mathrm{Im}(a_{MRef}(k\cdot\Delta z))\int_{(k-1)\cdot\Delta z}^{k\cdot\Delta z}F_j(z)dz\Bigg) +$$

$$i\sum_{k=1}^{L}\left(\mathrm{Re}(a_{MRef}(k\cdot\Delta z))\int_{(k-1)\cdot\Delta z}^{k\cdot\Delta z}C_j(z)dz - \right.$$

$$\left.\mathrm{Im}(a_{MRef}(k\cdot\Delta z))\int_{(k-1)\cdot\Delta z}^{k\cdot\Delta z}D_j(z)dz\right)$$

$$Y_{jRef} = \sum_{k=1}^{L}\left(\mathrm{Re}(a_{MRef}(k\cdot\Delta z))\int_{(k-1)\cdot\Delta z}^{k\cdot\Delta z}E_j(z)dz - \right.$$
[Eq. 30]

$$\mathrm{Im}(a_{MRef}(k\cdot\Delta z))\int_{(k-1)\cdot\Delta z}^{k\cdot\Delta z}F_j(z)dz + i\bigg(\mathrm{Re}(a_{MRef}(k\cdot\Delta z))$$

$$\left.\int_{(k-1)\cdot\Delta z}^{k\cdot\Delta z}C_j(z)dz - \mathrm{Im}(a_{MRef}(k\cdot\Delta z))\int_{(k-1)\cdot\Delta z}^{k\cdot\Delta z}D_j(z)dz\bigg)\right)$$

$$Y_{jRef} = \sum_{k=1}^{L}\left(\mathrm{Re}(a_{MRef}(k\cdot\Delta z))\int_{(k-1)\cdot\Delta z}^{k\cdot\Delta z}(E_j(z)+iC_j(z))dz - \right.$$
[Eq. 31]

$$\left.\mathrm{Im}(a_{MRef}(k\cdot\Delta z))\int_{(k-1)\cdot\Delta z}^{k\cdot\Delta z}(F_j(z)+iD_j(z))dz\right)$$

$$Y_{jRef} =$$
[Eq. 32]

$$\sum_{k=1}^{L}\left(4\mathrm{Re}(A_R)\mathrm{Re}(a_{MRef}(k\cdot\Delta z))\int_{(k-1)\cdot\Delta z}^{k\cdot\Delta z}(S13_j(z)+iS24_j(z))dz + \right.$$

$$\left.4\mathrm{Im}(A_R)\mathrm{Im}(a_{MRef}(k\cdot\Delta z))\int_{(k-1)\cdot\Delta z}^{k\cdot\Delta z}(S13_j(z)+iS24_j(z))dz\right)$$

with.

$$S13_j(z) = \sum_{p=1}^{N}\Pi_j(p)$$
[Eq. 33]

$$\left(\int_{pT_{US}}^{pT_{US}+T_{US}/4}\cos(\omega_{US}(t-z/\upsilon_{US})+\pi\Phi_j(t-z/\upsilon_{US}+\delta_j))dt - \right.$$

$$\left.\int_{pT_{US}+T_{US}/2}^{pT_{US}+3T_{US}/4}\cos(\omega_{US}(t-z/\upsilon_{US})+\pi\Phi_j(t-z/\upsilon_{US}+\delta_j))dt\right) \text{ and:}$$

$$S24_j(z) = \sum_{p=1}^{N}\Pi_j(p)$$
[Eq. 34]

$$\left(\int_{pT_{US}+T_{US}/4}^{pT_{US}+T_{US}/2}\cos(\omega_{US}(t-z/\upsilon_{US})+\pi\Phi_j(t-z/\upsilon_{US}+\delta_j))dt - \right.$$

-continued $$\int_{pT_{US}+3T_{US}/4}^{pT_{US}+T_{US}} \cos(\omega_{US}(t-z/\upsilon_{US})+\pi\Phi_j(t-z/\upsilon_{US}+\delta_j))dt)$$

One then rewrites:

$$Y_{j\,Ref} = \qquad\qquad\qquad\qquad\qquad\qquad\qquad\text{[Eq. 35]}$$

$$\sum_{k=1}^{L}\left((4\text{Re}(A_R)\text{Re}(a_{M\,Ref}(k\cdot\Delta z))+4\text{Im}(A_R)\text{Im}(a_{M\,Ref}(k\cdot\Delta z)))\right.$$

$$\left.\int_{(k-1)\cdot\Delta z}^{k\cdot\Delta z}(S13_j(z)+iS24_j(z))dz\right)$$

Having identified the relation between the measurements and the absorption profile according to equation 35, the following matrix relation can be established:

$$Y = \mathcal{A}_{RE}\text{Re}(a_M) + \mathcal{A}_{Im}\text{Im}(a_M) \qquad\text{[Eq. 36]}$$

where $A_{Re}$ and $A_{Im}$ are two matrices each having M rows and L columns, and $a_M$ is a vector of L rows and one column having its modulus corresponding to the desired absorption profile.

Term $A_{Re\,j,k}$ designates the value of the row of rank j and of the column of rank k in matrix $A_{Re}$, and term $A_{Im\,j,k}$ designates the value of the row of rank j and of the column of rank k in matrix $A_{Im}$.

The values $A_{Re\,j,k}$ and $A_{Im\,j,k}$ of matrices $A_{Re}$ and $A_{Im}$ can be expressed as follows:

$$\mathcal{A}_{Re\,j,k} = 4\,\text{Re}(A_R)\text{Re}(a_{M\,Ref}(k\cdot\Delta z))\int_{(k-1)\cdot\Delta z}^{k\cdot\Delta z}(S13_j(z)+iS24_j(z))dz \qquad\text{[Eq. 37]}$$

and:

$$\mathcal{A} = 4\,\text{Im}(A_R)\text{Im}(a_{M\,Ref}(k\cdot\Delta z))\int_{(k-1)\cdot\Delta z}^{k\cdot\Delta z}(S13_j(z)+iS24_j(z))dz \qquad\text{[Eq. 38]}$$

Matrices $A_{Re\,j,k}$ and $A_{Im\,j,k}$ are the transitions matrices of the system. Considering M measurements (j varies from 1 to M), the matrices are each formed of M rows and L columns, L corresponding to the number of points of the absorption profile. Conversely to the solution discussed in relation with FIGS. 3 and 4, in the embodiment of FIG. 4, the number M of performed measurements may be smaller than the number L of points of the absorption profile which is desired to be reconstructed.

One thus as a model such that:

$$Y = Fct(a_M) = \varepsilon \qquad\text{[Eq. 39]}$$

where Y is a vector of M imaginary numbers $Y_j$ respectively corresponding to the M measurements performed by the sensor, Fct is a function of absorption profile $a_M$, and □ is an error term which will be desired to be minimized.

An estimate of absorption profile $a_M$ is thus desired, which is noted as follows:

$$\widehat{a_M} \qquad\text{[Eq. 40]}$$

For this purpose, it is desired to solve the following error minimization problem:

$$\operatorname*{argmin}_{\widehat{a_M}}(\|Y - Fct(\widehat{a_M})\|_2^2) \qquad\text{[Eq. 4]}$$

This problem having an infinite number of solutions, a regularization term enabling to solve it is added.

Known transition matrices $A_{Re\,j,k}$ and $A_{Im\,j,k}$, the reconstruction of the absorption profile defined by vector $a_M$ may be performed by minimizing the following cost function:

$$\operatorname*{argmin}_{\widehat{a_M}}(\|(\mathcal{A}_{Re}\text{Re}(\widehat{a_M}) + \mathcal{A}_{Im}\text{Im}(\widehat{a_M})) - Y\|_2 + \lambda\|\psi|\widehat{a_M}|\|_1) \qquad\text{[Eq. 42]}$$

where ψ is a function defining a reconstruction constraint on the modulus of vector $a_M$, corresponding to supposed properties of the signal to be reconstructed. Coefficient λ enables to weight the contribution of the reconstruction constraint in the global cost function. In this example, the constraint is defined from standard 1 of function ψ, multiplied by the estimate of absorption profile $a_M$. As an example, function ψ is a filter bank formed from a differential operator along the propagation axis of the acoustic, duplicated at different scales for each of positions z. More generally, any other method of synthesis of the reconstruction constraint, enabling to take into account supposed properties of the desired signal, may be used.

Based on this equation, a vector $a_M$ having its module corresponding to the desired absorption profile is reconstructed.

The resolution of the minimization problem defined by equation 42 is for example implemented by an electronic processing circuit (not shown in the drawing), for example comprising a microprocessor. The processing circuit may be integrated to sensor 109, or external to sensor 109.

It should be noted that in the embodiment of FIG. 5, transition matrix $A_{Re\,j,k}$ can be expressed as follows:

$$\mathcal{A}_{Re\,j,k} = \int_{(k-1)\cdot\Delta z}^{k\cdot\Delta z}\left(4\text{Re}(A_R)\text{Re}(a_{M\,Ref}(k\cdot\Delta z))\right. \qquad\text{[Eq. 43]}$$

$$\sum_{p=1}^{N}\Pi_j(p)\left(\left(\int_{pT_{US}}^{pT_{US}+T_{US}/4}\cos(\omega_{US}(t-z/\upsilon_{US})+\pi\Phi_j(t-z/\upsilon_{US}+\delta_j))\right.\right.$$

$$dt - \int_{pT_{US}+T_{US}/2}^{pT_{US}+3T_{US}/4}\cos(\omega_{US}(t-z/\upsilon_{US})+\pi\Phi_j(t-z/\upsilon_{US}+\delta_j))dt\right) +$$

$$i\left(\int_{pT_{US}+T_{US}/4}^{pT_{US}+T_{US}/2}\cos(\omega_{US}(t-z/\upsilon_{US})+\pi\Phi_j(t-z/\upsilon_{US}+\delta_j))dt - \right.$$

$$\int_{pT_{US}+3T_{US}/4}^{pT_{US}+T_{US}}\cos(\omega_{US}(t-z/\upsilon_{US})+\pi\Phi_j(t-z/\upsilon_{US}+\delta_j))$$

$$\left.\left.\left.dt\right)\right)\right)dz \text{ that is:}$$

$$\mathcal{A}_{Re\,j,k} = \qquad\text{[Eq. 44]}$$

$$\int_{(k-1)\cdot\Delta z}^{k\cdot\Delta z}\left(4\text{Re}(A_R)\text{Re}(a_{M\,Ref}(k\cdot\Delta z))\sum_{p=1}^{N}\Pi_j(p)\Gamma_j(p,z)\right)dz \text{ with:}$$

$$\Gamma_j(p,z) = \qquad\text{[Eq. 45]}$$

$$\left(\left(\int_{pT_{US}}^{pT_{US}+T_{US}/4}\cos(\omega_{US}(t-z/\upsilon_{US})+\pi\Phi_j(t-z/\upsilon_{US}+\delta_j))dt - \right.\right.$$

$$\int_{pT_{US}+T_{US}/2}^{pT_{US}+3T_{US}/4}\cos(\omega_{US}(t-z/\upsilon_{US})+\pi\Phi_j(t-z/\upsilon_{US}+\delta_j))dt\right) +$$

$$i\left(\int_{pT_{US}+T_{US}/4}^{pT_{US}+T_{US}/2}\cos(\omega_{US}(t-z/\upsilon_{US})+\pi\Phi_j(t-z/\upsilon_{US}+\delta_j))dt - \right.$$

-continued $$\int_{pT_{US}+3T_{US}/4}^{pT_{US}+T_{US}} \cos(\omega_{US}(t-z/\upsilon_{US})+\pi\Phi_j(t-z/\upsilon_{US}+\delta_j))dt)\Big)$$

The combination of Π and Γ of F provides a Rademacher law, similar to a Bernoulli law, having its sum tending, according to the Moivre Laplace theorem, towards a random Gaussian distribution variable. The coefficients of transition matrix $A_{Re\,j,k}$ are asymptotically related to drawings from a Gaussian distribution, allowing a reconstruction of compressive acquisition type.

A similar line of reasoning applies concerning transition matrix $A_{Im\,j,k}$.

Although an example of operation based on a demodulation with K=4 phases of the modulated light signal has been described hereabove, the embodiment of FIG. 5 is not limited to this specific case. As a variation, the demodulation may be performed on any other number K of phases greater than or equal to 2. It will be within the abilities of those skilled in the art to accordingly adapt the pixel circuits, particularly to acquire a number of samples different from four at each modulation period $T_{US}$ of acquisition phase $T_{acq}$. The formulas of reconstruction of the real and imaginary parts of the complex field of the object beam may be adapted accordingly.

Further, although, in the example described hereabove in relation with FIG. 5, a phase of the acoustic marking wave which is zero at the origin has been considered, the described embodiments are not limited to this specific case. As a variation, the above-described calculations may be resumed with the addition of a non-zero phase φ such that:

$$E_s(t)=A_De^{i\omega_L t}+ \\ \int_z a_M(z)e^{-i\omega_{US}z/\upsilon_{US}}e^{i((\omega_L+\omega_{US})t+\Phi(t-z/\upsilon_{US}+\delta\phi)}dz+ \\ \int_z a_M(z)e^{i\omega_{US}z/\upsilon_{US}}e^{i((\omega_L-\omega_{US})t-\phi(t-z/\upsilon_{US}+\delta)+\phi)}dz$$

[Eq. 46]

Figure 6:
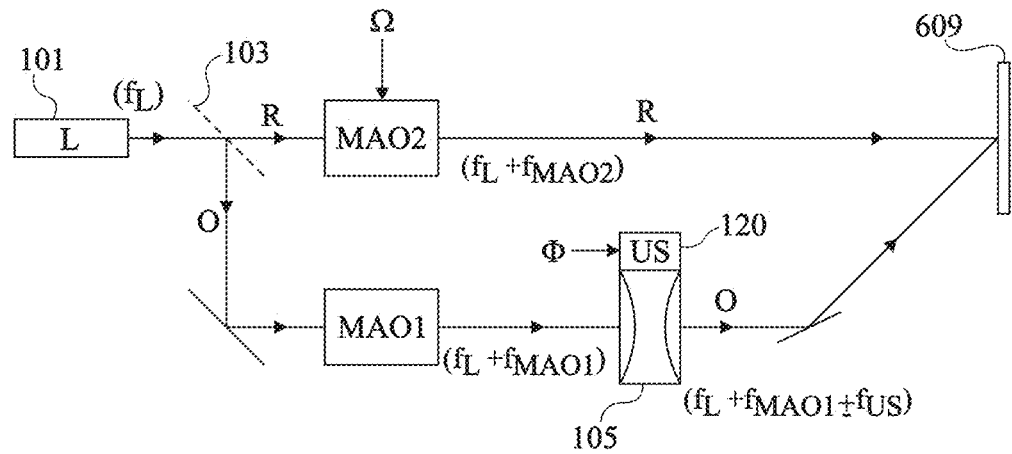
FIG. 6 schematically shows an example of an acoustic-optical imaging system according to a second embodiment.

FIG. 6 schematically shows an example of an acoustic-optical imaging system according to a second embodiment.

The system of FIG. 6 comprises, as in the previous examples, a light source 101 (L) capable of generating a coherent light beam of frequency $f_L$, and a splitter 103 enabling to divide the beam generated by source 101 into an object beam O and a reference beam R. In the system of FIG. 6, at the output of separator 103, object beam O is modulated by a first acoustic-optical modulator MAO1 shifting its frequency by a value $f_{MAO1}$, and reference beam R is modulated by a second acoustic-optical modulator MAO2 shifting its frequency by a value $f_{MAO2}$ different from value $f_{MAO1}$. The system is arranged so that the object beam, of frequency $f_L+f_{MAO1}$, illuminates the object or sample 105 to be analyzed, and that the reference beam, of frequency $f_L+f_{MAO2}$, does not cross sample 105.

As in the previous examples, the reference beam and the object beam reflected or transmitted by object 105 are then projected onto an image sensor 609, to generate an interference pattern in the acquisition plane of the sensor.

Further, as in the previous examples, a portion of sample 105 is excited by a focused ultrasound wave of frequency $F_{US}$. As a result, the frequency of the rays of the object beam running through the excited portion of the sample is shifted to value $f_L+f_{MAO1}+F_{US}$ or $f_L+f_{MAO1}-F_{US}$, while the frequency of the rays of the object beam running through the non-excited portions of the sample remains at value $f_L+f_{MAO1}$. As previously, it is desired to measure the energy carried by the photons marked by the acoustic wave of frequency $F_{US}$, to deduce therefrom information relative to light absorption in the marking area.

In operation, sensor 609 sees an interference pattern having a beat frequency $f_B$ equal to the absolute value of difference $f_{MAO1}+F_{US}-f_{MAO2}$.

Conversely to the previously-described sensor 109, comprising an electronic demodulation device, for example in the form of an integration circuit with K switched capacitors per pixel, synchronously rated at a frequency equal to K times the frequency $F_{US}$ of the acoustic marking wave, in the embodiment of FIG. 6, sensor 609 is a standard sensor, for example comprising an integration circuit with a single capacitor per pixel. In this example, the frequency $F_C$ of image acquisition by sensor 609 is equal to K times the beat frequency $f_B$ of the system. The assembly with two acoustic-optical modulators MAO1 and MAO2 of FIG. 6 enables to use a sensor 609 having a relatively low acquisition frequency $F_C$, for example, in the range from 20 Hz to 20 kHz, which corresponds to the typical acquisition frequencies of usual image sensors.

Usual acoustic-optical modulators may typically shift the frequency of a light beam by a value in the order from a few MHz to a few tens of MHz, for example, by a value in the range from 5 to 100 MHz. The marking ultrasound wave applied to sample 105 causes a frequency shift of the light crossing the excited portion of the object by a value for example in the range from 1 to 15 MHz. Modulators MAO1 and MAO2 are selected to obtain a beat frequency $f_B$ compatible with the use of a low-frequency sensor, for example, such that frequency $F_C=K*f_B$ is in the range from 20 Hz to 20 kHz.

As a numerical illustration, and without this being limiting, in the system of FIG. 6, sensor 609 may have an acquisition frequency $F_C$ of 8 kHz, and the frequency shifts $f_{MAO1}$, $f_{MAO2}$ and $F_{US}$ introduced by modulators MAO1 and MAO2 and by the ultrasound wave of excitation of sample 105 may respectively be 77.001 MHz, 79.999 MHz, and 3 MHz, to obtain a beat frequency $f_B=f_{MAO1}+F_{US}-f_{MAO2}=2$ kHz=$F_C/4$ (considering case K=4).

As in the embodiment of FIG. 5, it is provided to reconstruct an absorption profile of the marking column, having an axial resolution L, based on a series of M measurements, L and M being integers greater than or equal to 2.

During each measurement, a first random or pseudo-random sequence Φ of phase jumps is applied to the acoustic marking signal, identically or similarly to what has been described in the example of FIG. 5.

During the acquisition phase, having a duration $T_{acq}=T_B=1/f_B$, K images are successively acquired by means of sensor 609. For each of the M measurements, a set of K values corresponding to the four phases of beat period $T_B$ is thus obtained for each pixel. For simplification, case K=4 will be considered hereafter and references I0, I1, I2, and I3 will be used to designate the four samples acquired by a pixel during a same acquisition phase $T_{acq}$ (corresponding to the values of the pixel in the 4 images successively acquired during phase $T_{acq}$).

As in the embodiment of FIG. 5, it is provided, for each measurement, to apply to the measured signal a demodulation sequence Ω, in the form of a random or pseudo-random phase jump sequence which is not correlated to sequence Φ.

The embodiment of FIG. 6 differs from the embodiment of FIG. 5 in that, in the embodiment of FIG. 6, instead of being applied in the electronic domain by a demodulation device integrated to the sensor, demodulation sequence Ω is applied in the optical domain, via the acoustic-optical modulator MAO2 placed on reference arm R. In other words, in this example, demodulation sequence Ω is a random or pseudo-random sequence directly applied to reference beam R, before the interference of beam R with object beam O.

The signal s(t) measured at the level of a pixel of sensor 609 at the end of the interference between the object arm and the reference arm is given by the following equation:

$$s(t)=|E_r(t)=E_s(t)|^2 \qquad [\text{Eq. 47}]$$

with:

$$E_r(t)=A_R e^{i(\omega_R t=n(t-\delta))} \qquad [\text{Eq. 48}]$$

and:

$$E_s(t)=A_D e^{i\omega_O t}+\int_z a_M(z)e^{i(\omega_O t+\omega_{US}(t-z/\upsilon_{US})+\Phi((t-z/\upsilon_{US}))}dz+$$
$$\int_z a_M(z)e^{i(\omega_O t-\omega_{US}(t-z/\upsilon_{US})-\Phi((t-z/\upsilon_{US}))}dz \qquad [\text{Eq. 49}]$$

that is:

$$E_s(t)=A_D e^{i\omega_O t}+\int_z a_{M+}(z)e^{i((\omega_O+\omega_{US})t+\Phi((t-z/\upsilon_{US}))}dz+$$
$$\int_z a_{M-}(z)e^{i((\omega_O-\omega_{US})t-\Phi((t-z/\upsilon_{US}))}dz \qquad [\text{Eq. 50}]$$

where:

$$a_{M+}(z)=a_M(z)e^{-i\omega_{US}z/\upsilon_{US}} \qquad [\text{Eq. 51}]$$

$$a_{M-}(z)=a_M(z)e^{i\omega_{US}z/\upsilon_{US}} \qquad [\text{Eq. 52}]$$

and where:

$$\omega_R=2\pi(f_L+f_{MAO2}) \qquad [\text{Eq. 53}]$$

$$\omega_O=2\pi(f_L+f_{MAO1}) \qquad [\text{Eq. 54}]$$

$$\omega_R-\omega_O=\omega_{US}-\omega_{CAM} \qquad [\text{Eq. 55}]$$

$$\omega_{CAM}=2\pi F_{CAM} \qquad [\text{Eq. 56}]$$

where $F_{CAM}$ designates the acquisition frequency of the system, such that $F_{CAM}=1/T_{acq}=F_C/4$.

Equation 50 can then be rewritten as follows:

$$E_s(t)=A_D e^{i\omega_O t}+\int_z a_{M+}(Z)e^{i((\omega_R+\omega_{CAM})t+\Phi(t-Z/\upsilon_{US}))}dz+$$
$$\int_z a_{M-}(z)e^{i((\omega_R-2\omega_{US}+\omega_{CAM})t-\Phi(t-Z/\upsilon_{US}))}dz \qquad [\text{Eq. 57}]$$

whereby:

$$s(t)=\left|e^{i(\omega_R t+\Omega(t-\delta))}\right|\cdot\left|\begin{array}{l}A_R+A_D e^{i((\omega_O-\omega_R)t-\Omega(t-\delta))}+\\ \int_z a_{M+}(z)e^{i\binom{(\omega_R+\omega_{CAM})t+\\ \Phi(t-z/\upsilon_{US})-\\ \omega_R t-\Omega(t-\delta)}}dz+\\ \int_z a_{M-}(z)e^{i\binom{(\omega_R-2\omega_{US}+\omega_{CAM})t\\ -\Phi(t-z/\upsilon_{US})-\\ \omega_R t-\Omega(t-\delta)}}dz\end{array}\right|^2 \qquad [\text{Eq. 58}]$$

$$s(t)=\left|\begin{array}{l}A_R+A_D e^{i((\omega_O-\omega_R)t-\Omega(t-\delta))}+\\ \int_z a_M(z)e^{i(\omega_{CAM}t-\omega_{US}z/\upsilon_{US}+\Phi(t-z/\upsilon_{US})-\Omega(t-\delta))}dz+\\ \int_z a_{M-}(z)e^{i\binom{(\omega_{CAM}-2\omega_{US})t+\omega_{US}z/\upsilon_{US}-\\ \Phi(t-z/\upsilon_{US})-\Omega(t-\delta)}}dz\end{array}\right|^2 \qquad [\text{Eq. 59}]$$

At the level of sensor 609, K=4 images are successively acquired with an acquisition duration $T_{CAM}/4$ per image (with $T_{CAM}=1/F_{CAM}$). Paths I and Q can be expressed as follows:

$$I=\int_0^{T_{CAM}/4}s(t)dt-\int_{T_{CAM}/2}^{3T_{CAM}/4}s(t)dt \qquad [\text{Eq. 60}]$$

$$Q=\int_{T_{CAM}/4}^{T_{CAM}/2}s(t)dt-\int_{3T_{CAM}/4}^{T_{CAM}}s(t)dt \qquad [\text{Eq. 61}]$$

Functions F and G are defined, such that:

$$F(z,t)=e^{i(\omega_{CAM}t-\omega_{US}z/\upsilon_{US}+\Phi(t-z/\upsilon_{US})-\Omega(t-\delta))} \qquad [\text{Eq. 62}]$$

$$G(z,t)=e^{i((\omega_{CAM}-2\omega_{US})t+\omega_{US}z/\upsilon_{US}-\Phi((t-z/\upsilon_{US})-\Omega(t-\delta))} \qquad [\text{Eq. 63}]$$

One then has:

$$I=\int_0^{T_{CAM}/4}\left(\left(\text{Re}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2+\right.$$
$$\left.\left(\text{Im}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2\right)dt-$$
$$\int_{T_{CAM}/2}^{3T_{CAM}/4}\left(\left(\text{Re}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2+\right.$$
$$\left.\left(\text{Im}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2\right)dt \qquad [\text{Eq. 64}]$$

$$Q=\int_{T_{CAM}/4}^{T_{CAM}/2}\left(\left(\text{Re}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2+\right.$$
$$\left.\left(\text{Im}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2\right)dt-$$
$$\int_{3T_{CAM}/4}^{T_{CAM}}\left(\left(\text{Re}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2+\right.$$
$$\left.\left(\text{Im}\left(\begin{array}{l}A_R+A_D e^{i((\omega_O-\omega_R)t-\Omega(t-\delta))}+\\ \int_z a_M(z)(F(z,t)+G(z,t))dz\end{array}\right)\right)^2\right)dt \qquad [\text{Eq. 65}]$$

As in the embodiment of FIG. 5, the terms which do not depend on $A_R$ are neglected, the energy carried by the reference arm widely dominating over the other terms. Further, the terms depending on $A_D$ are here neglected. Due to their high-frequency component independent from $\omega_{CAM}$, these terms will indeed be averaged over the integration time of each image, in the order of $T_{CAM}/4$, and the residual value will be taken to zero by the four-phase demodulation (difference I0–I2 and I1–I3). One then obtains:

$$I=\int_0^{T_{CAM}/4}\left(2\text{Re}(A_R)\text{Re}\left(\int_z a_M(z)(F(z,t)+G(z,t))dz\right)+\right.$$
$$\left.2\text{Im}(A_R)\text{Im}\left(\int_z a_M(z)(F(z,t)+G(z,t))dz\right)\right)dt-$$
$$\int_{T_{CAM}/2}^{3T_{CAM}/4}\left(2\text{Re}(A_R)\text{Re}\left(\int_z a_M(z)(F(z,t)+G(z,t))dz\right)+\right.$$
$$\left.2\text{Im}(A_R)\text{Im}\left(\int_z a_M(z)(F(z,t)+G(z,t))dz\right)\right)dt \qquad [\text{Eq. 66}]$$

$$Q=\int_{T_{CAM}/4}^{T_{CAM}/2}\left(2\text{Re}(A_R)\text{Re}\left(\int_z a_M(z)(F(z,t)+G(z,t))dz\right)+\right.$$
$$\left.2\text{Im}(A_R)\text{Im}\left(\int_z a_M(z)(F(z,t)+G(z,t))dz\right)\right)dt-$$
$$\int_{3T_{CAM}/4}^{T_{CAM}}\left(2\text{Re}(A_R)\text{Re}\left(\int_z a_M(z)(F(z,t)+G(z,t))dz\right)+\right.$$
$$\left.2\text{Im}(A_R)\text{Im}\left(\int_z a_M(z)(F(z,t)+G(z,t))dz\right)\right)dt \qquad [\text{Eq. 67}]$$

whereby:

$$I = \int_0^{T_{CAM}/4}\left(2\text{Re}(A_R)\int_z\Big(\text{Re}(a_M(z))\text{Re}(F(z,t)+G(z,t))-\text{Im}(a_M(z))\text{Im}(F(z,t)+G(z,t))\Big)dz + 2\text{Im}(A_R)\int_z\Big(\text{Re}(a_M(z))\text{Im}(F(z,t)+G(z,t))+\text{Im}(a_M(z))\text{Re}(F(z,t)+G(z,t))\Big)dz\right)dt - \int_{T_{CAM}/2}^{3T_{CAM}/4}\left(2\text{Re}(A_R)\int_z\Big(\text{Re}(a_M(z))\text{Re}(F(z,t)+G(z,t))-\text{Im}(a_M(z))\text{Im}(F(z,t)+G(z,t))\Big)dz + 2\text{Im}(A_R)\int_z\Big(\text{Re}(a_M(z))\text{Im}(F(z,t)+G(z,t))+\text{Im}(a_M(z))\text{Re}(F(z,t)+G(z,t))\Big)dz\right)dt$$

[Eq. 68]

$$Q = \int_{T_{CAM}/4}^{T_{CAM}/2}\left(2\text{Re}(A_R)\int_z\Big(\text{Re}(a_M(z))\text{Re}(F(z,t)+G(z,t))-\text{Im}(a_M(z))\text{Im}(F(z,t)+G(z,t))\Big)dz + 2\text{Im}(A_R)\int_z\Big(\text{Re}(a_M(z))\text{Im}(F(z,t)+G(z,t))+\text{Im}(a_M(z))\text{Re}(F(z,t)+G(z,t))\Big)dz\right)dt - \int_{3T_{CAM}/4}^{T_{CAM}}\left(2\text{Re}(A_R)\int_z\Big(\text{Re}(a_M(z))\text{Re}(F(z,t)+G(z,t))-\text{Im}(a_M(z))\text{Im}(F(z,t)+G(z,t))\Big)dz + 2\text{Im}(A_R)\int_z\Big(\text{Re}(a_M(z))\text{Im}(F(z,t)+G(z,t))+\text{Im}(a_M(z))\text{Re}(F(z,t)+G(z,t))\Big)dz\right)dt$$

[Eq. 69]

Terms I and Q are then rewritten in the form described in relation with FIG. 5:

$$I = \int_z \text{Re}(a_M(z))\left(\int_0^{T_{CAM}/4}(2\text{Re}(A_R)\text{Re}(F(z,t)+G(z,t))+2\text{Im}(A_R)\text{Im}(F(z,t)+G(z,t)))dt - \int_{T_{CAM}/2}^{3T_{CAM}/4}(2\text{Re}(A_R)\text{Re}(F(z,t)+G(z,t))+2\text{Im}(A_R)\text{Im}(F(z,t)+G(z,t)))dt\right)dz - \int_z \text{Im}(a_M(z))\left(\int_0^{T_{CAM}/4}(2\text{Re}(A_R)\text{Im}(F(z,t)+G(z,t))-2\text{Im}(A_R)\text{Re}(F(z,t)+G(z,t)))dt - \int_{T_{CAM}/2}^{3T_{CAM}/4}(2\text{Re}(A_R)\text{Im}(F(z,t)+G(z,t))-2\text{Im}(A_R)\text{Re}(F(z,t)+G(z,t)))dt\right)dz$$

[Eq. 70]

$$Q = \int_z \text{Re}(a_M(z))\left(\int_{T_{CAM}/4}^{T_{CAM}/2}(2\text{Re}(A_R)\text{Re}(F(z,t)+G(z,t))+2\text{Im}(A_R)\text{Im}(F(z,t)+G(z,t)))dt - \int_{3T_{CAM}/4}^{T_{CAM}}(2\text{Re}(A_R)\text{Re}(F(z,t)+G(z,t))+2\text{Im}(A_R)\text{Im}(F(z,t)+G(z,t)))dt\right)dz -$$

[Eq. 71]

$$\int_z \text{Im}(a_M(z))\left(\int_{T_{CAM}/4}^{T_{CAM}/2}(2\text{Re}(A_R)\text{Im}(F(z,t)+G(z,t))-2\text{Im}(A_R)\text{Re}(F(z,t)+G(z,t)))dt - \int_{3T_{CAM}/4}^{T_{CAM}}(2\text{Re}(A_R)\text{Im}(F(z,t)+G(z,t))-2\text{Im}(A_R)\text{Re}(F(z,t)+G(z,t)))dt\right)dz$$

For each measurement of rank j, these equations can be rewritten as follows:

$$Q_j = \int_z \text{Re}(a_M(z))C_j(z)dz - \int_z \text{Im}(a_M(z))D_j(z)dz \quad \text{[Eq. 72]}$$

$$I_j = \text{Re}(a_M(z))E_j(z)dz - \int_z \text{Im}(a_M(z))F_j(z)dz \quad \text{[Eq. 73]}$$

with:

$$C_j(z) = \int_{T_{CAM}/4}^{T_{CAM}/2}(2\text{Re}(A_R)\text{Re}(F_j(z,t)+G_j(z,t))+2\text{Im}(A_R)\text{Im}(F_j(z,t)+G_j(z,t)))dt - \int_{3T_{CAM}/4}^{T_{CAM}}(2\text{Re}(A_R)\text{Re}(F_j(z,t)+G_j(z,t))+2\text{Im}(A_R)\text{Im}(F_j(z,t)+G_j(z,t)))dt$$

[Eq. 74]

$$D_j(z) = \int_{T_{CAM}/4}^{T_{CAM}/2}(2\text{Re}(A_R)\text{Im}(F_j(z,t)+G_j(z,t))-2\text{Im}(A_R)\text{Re}(F_j(z,t)+G_j(z,t)))dt - \int_{3T_{CAM}/4}^{T_{CAM}}(2\text{Re}(A_R)\text{Im}(F_j(z,t)+G_j(z,t))-2\text{Im}(A_R)\text{Re}(F_j(z,t)+G_j(z,t)))dt$$

[Eq. 75]

$$E_j(z) = \int_0^{T_{CAM}/4}(2\text{Re}(A_R)\text{Re}(F_j(z,t)+G_j(z,t))+2\text{Im}(A_R)\text{Im}(F_j(z,t)+G_j(z,j)))dt - \int_{T_{CAM}/2}^{3T_{CAM}/4}(2\text{Re}(A_R)\text{Re}(F_j(z,t)+G_j(z,t))+2\text{Im}(A_R)\text{Im}(F_j(z,t)+G_j(z,t)))dt$$

[Eq. 76]

$$F_j(z) = \int_0^{T_{CAM}/4}(2\text{Re}(A_R)\text{Im}(F_j(z,t)+G_j(z,t))-2\text{Im}(A_R)\text{Re}(F_j(z,t)+G_j(z,t)))dt - \int_{T_{CAM}/2}^{3T_{CAM}/4}(2\text{Re}(A_R)\text{Im}(F_j(z,t)+G_j(z,t))-2\text{Im}(A_R)\text{Re}(F_j(z,t)+G_j(z,j)))dt$$

[Eq. 77]

and:

$$F_j(t,z) = e^{i(\omega_{CAM}t-\omega_{US}z/\upsilon_{US}+\Phi_j(t-z/\upsilon_{US})-\Omega_j(t-\delta))} \quad \text{[Eq. 78]}$$

$$G_j(t,z) = e^{i((\omega_{CAM}-2\omega_{US})t+\omega_{US}z/\upsilon_{US}-\Phi_j(t-z/\upsilon_{US})-\Omega_j(t-\delta))} \quad \text{[Eq. 79]}$$

Each of the M obtained measurements can be rewritten as $Y_j = I_j + iQ_j$, with:

$$Q_j = \sum_{k=1}^{L}\left(\text{Re}(a_M(k\cdot\Delta z))\int_{(k-1)\cdot\Delta z}^{k\cdot\Delta z}C_j(z)dz - \text{Im}(a_M(k\cdot\Delta z))\int_{(k-1)\cdot\Delta z}^{k\cdot\Delta z}D_j(z)dz\right)$$

[Eq. 80]

-continued $$I_j = \sum_{k=1}^{L} \left( \text{Re}(a_M(k \cdot \Delta z)) \int_{(k-1)\Delta z}^{k \cdot \Delta z} E_j(z)dz - \text{Im}(a_M(k \cdot \Delta z)) \int_{(k-1)\Delta z}^{k \cdot \Delta z} F_j(z)dz \right) \quad [\text{Eq. 81}]$$

This provides the form of I and Q defined in the example of FIG. 5 (equations 25 and 26). The same method of construction of transition matrices as in the previous example can thus be used (equations 27 to 38), by replacing term G(t,z) with F(z,t)+G(z,t), followed by the same method of reconstruction of absorption profile $a_M$ (equation 42).

The system described in relation with FIG. 6 enables, for each of the M measurements of the phase of acquisition of the absorption profile, to perform the four-phase demodulation by means of 4 images acquired via a standard camera (with an acquisition period of $T_{CAM}/4$ for each image). Such a technique further enables to use high acoustic modulation frequencies $F_{US}$.

Figure 7:
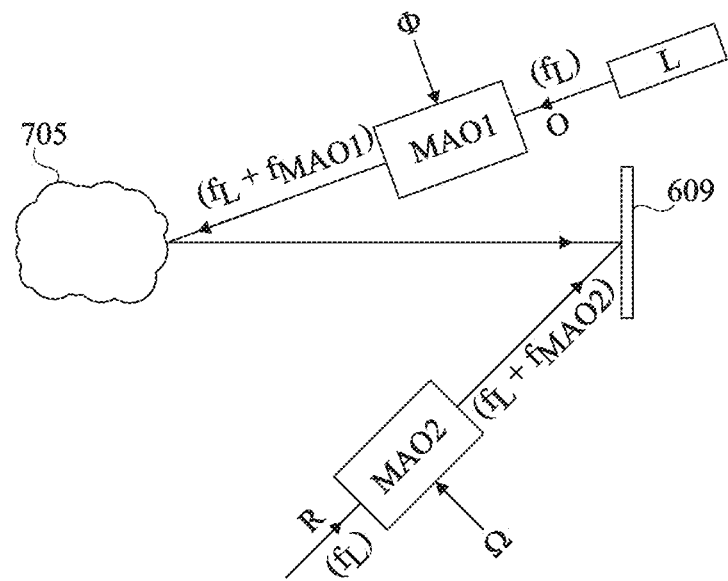
FIG. 7 schematically shows an example of an acoustic-optical imaging system according to a third embodiment.

FIG. 7 schematically shows an example of an acoustic-optical imaging system according to a third embodiment.

In this embodiment, it is provided to extend the method described in relation with FIG. 6 to applications of depth measurement in a scene.

In the system of FIG. 7, sample 105 is replaced with a reflective object 705, corresponding to a scene where depth information is desired to be measured. In this example, no local marking of a portion of the object beam is provided. In other words, no ultrasound transducer arranged to apply a local mechanical wave to a portion of the scene is provided. In FIG. 7, for simplification, the means for splitting the beam emitted by the source into an object beam and a reference beam have not been shown.

Modulation sequence $\Phi$ is applied to the object beam upstream of scene 705, via acoustic-optical modulator MAO1. Demodulation sequence $\Omega$ is applied to the reference beam via acoustic-optical modulator MAO2.

Modulators MAO1 and MAO2 are selected to obtain a beat frequency $f_B$ (here equal to the absolute value of difference $f_{MAO1}-f_{MAO2}$) compatible with the use of a low-frequency sensor, for example, such that frequency $F_C=K^*f_B$ is in the range from 20 Hz to 20 kHz.

As a numerical illustration, and without this being limiting, in the system of FIG. 7, sensor 609 may have an acquisition frequency $F_C$ of 8 kHz, and the frequency shifts $f_{MAO1}$ and $f_{MAO2}$ introduced by modulators MAO1 and MAO2 may respectively be 80.001 MHz, 79.999 MHz, to obtain a beat frequency $f_B=f_{MAO1}-f_{MAO2}=2$ kHz=$F_C/4$ (considering case K=4).

In the embodiment of FIG. 7, the modulus of the measured vector $a_M$ corresponds to the absorption profile of the source beam along the optical path between the output of modulator MAO1 and sensor 609, mainly corresponding to the absorption of the reflective elements of scene 705 along the optical propagation path (of ballistic nature in this case).

The signal s(t) measured at the level of a pixel of sensor 609 at the end of the interference between the object arm and the reference arm is given by the following equation:

$$S(t)=|E_r(t)+E_s(t)|^2 \quad [\text{Eq. 82}]$$

with:

$$E_r(t)=A_R e^{i(\omega_R t+\Omega(t-\delta))} \quad [\text{Eq. 83}]$$

and:

$$E_s(t)=\int_z a_M(z) e^{i(\omega_O(t-z/\upsilon_L)+\Phi(t-z/\upsilon_L))} dz \quad [\text{Eq. 84}]$$

$\upsilon_L$ being the propagation speed of light in the medium, and:

$$\omega_R=2\pi(f_L+f_{MAO2}) \quad [\text{Eq. 85}]$$

$$\omega_O=2\pi(f_L+f_{MAO1}) \quad [\text{Eq. 86}]$$

$$\omega_R-\omega_O=\omega_{CAM} \quad [\text{Eq. 87}]$$

$$\omega_{CAM}=2\lambda F_{CAM} \quad [\text{Eq. 88}]$$

One then has:

$$s(t)=|e^{i(\omega_R t+\Omega(t-\delta))}| \cdot |A_R + \int_z a_M e^{i(\omega_O(t-z/\upsilon_L)+\Phi(t-z/\upsilon_L)-\omega_R t-\Omega(t-\delta))} dz|^2 \quad [\text{Eq. 89}]$$

$$S(t)=|A_R+\int_z a_M e^{i(\omega_{CAM} t-\omega_O z/\upsilon_L+\Phi(t-z/\upsilon_L)-\Omega(t-\delta))} dZ|^2 \quad [\text{Eq. 90}]$$

At the level of sensor 609, K=4 images are successively acquired with an acquisition duration $T_{CAM}/4$ per image. Paths I and Q may as previously be expressed as follows:

$$I=\int_0^{T_{CAM}/4} s(t)dt - \int_{T_{CAM}/2}^{3T_{CAM}/4} s(t)dt \quad [\text{Eq. 91}]$$

$$Q=\int_{T_{CAM}/4}^{T_{CAM}/2} s(t)dt - \int_{3T_{CAM}/4}^{T_{CAM}} s(t)dt \quad [\text{Eq. 92}]$$

A function F is defined, such that:

$$F(z,t)=e^{i(\omega_{CAM} t-\omega_O z/\upsilon_L+\Phi(t-z/\upsilon_L)-\Omega(t-\delta))} \quad [\text{Eq. 93}]$$

One then has:

$$I = \int_0^{T_{CAM}/4} \left( \left( \text{Re}\left(A_R + \int_z a_M F(z,t)dz\right) \right)^2 + \left( \text{Im}\left(A_R + \int_z a_M F(z,t)dz\right) \right)^2 \right) dt - \int_{T_{CAM}/2}^{3T_{CAM}/4} \left( \left( \text{Re}\left(A_R + \int_z a_M F(z,t)dz\right) \right)^2 + \left( \text{Im}\left(A_R + \int_z a_M F(z,t)dz\right) \right)^2 \right) dt \quad [\text{Eq. 94}]$$

$$Q = \int_{T_{CAM}/4}^{T_{CAM}/2} \left( \left( \text{Re}\left(A_R + \int_z a_M F(z,t)dz\right) \right)^2 + \left( \text{Im}\left(A_R + \int_z a_M F(z,t)dz\right) \right)^2 \right) dt - \int_{3T_{CAM}/4}^{T_{CAM}} \left( \left( \text{Re}\left(A_R + \int_z a_M F(z,t)dz\right) \right)^2 + \left( \text{Im}\left(A_R + \int_z a_M F(z,t)dz\right) \right)^2 \right) dt \quad [\text{Eq. 95}]$$

$$I = \int_0^{T_{CAM}/4} \left( 2\text{Re}(A_R)\text{Re}\left(\int_z a_M F(z,t)dz\right) + 2\text{Im}(A_R)\text{Im}\left(\int_z a_M F(z,t)dz\right) \right) dt - \int_{T_{CAM}/2}^{3T_{CAM}/4} \left( 2\text{Re}(A_R)\text{Re}\left(\int_z a_M F(z,t)dz\right) + 2\text{Im}(A_R)\text{Im}\left(\int_z a_M F(z,t)dz\right) \right) dt \quad [\text{Eq. 96}]$$

$$Q = \int_{T_{CAM}/4}^{T_{CAM}/2} \left( 2\text{Re}(A_R)\text{Re}\left(\int_z a_M F(z,t)dz\right) + 2\text{Im}(A_R)\text{Im}\left(\int_z a_M F(z,t)dz\right) \right) dt - \int_{3T_{CAM}/4}^{T_{CAM}} \left( 2\text{Re}(A_R)\text{Re}\left(\int_z a_M F(z,t)dz\right) + \right. \quad [\text{Eq. 97}]$$

-continued $$2\text{Im}(A_R)\text{Im}\left(\int_Z a_M F(z, t)dz\right)\bigg)dt$$

whereby:

$$I = \int_0^{T_{CAM}/4}\left(2\text{Re}(A_R)\right.$$

$$\iint_z \left(\text{Re}(a_M(z))\text{Re}(F(z, t)) - \text{Im}(a_M(z))\text{Im}(F(z, t))\right)dz +$$

$$2\text{Im}(A_R)\int_z (\text{Re}(a_M(z))\text{Im}(F(z, t)) + \text{Im}(a_M(z))\text{Re}(F(z, t)))dz\bigg)dt -$$

$$\int_{T_{CAM}/2}^{3T_{CAM}/4}\left(2\text{Re}(A_R)\int_z (\text{Re}(a_M(z))\text{Re}(F(z, t)) -\right.$$

$$\text{Im}(a_M(z))\text{Im}(F(z, t)))dz +$$

$$2\text{Im}(A_R)\int_z (\text{Re}(a_M(z))\text{Im}(F(z, t)) + \text{Im}(a_M(z))\text{Re}(F(z, t)))dz\bigg)dt$$

[Eq. 98]

$$Q =$$

[Eq. 99]

$$\int_{T_{CAM}/4}^{T_{CAM}/2}\left(2\text{Re}(A_R)\iint_z (\text{Re}(a_M(z))\text{Re}(F(z, t)) - \text{Im}(a_M(z))\text{Im}(F(z, t)))\right.$$

$$dz + 2\text{Im}(A_R)\int_z (\text{Re}(a_M(z))\text{Im}(F(z, t))\text{Im}(a_M(z))\text{Re}(F(z, t)))dz\bigg)dt -$$

$$\int_{3T_{CAM}/4}^{T_{CAM}}\left(2\text{Re}(A_R)\int_Z (\text{Re}(a_M(z))\text{Re}(F(z, t)) - \text{Im}(a_M(z))\text{Im}(F(z, t)))\right.$$

$$dz + 2\text{Im}(A_R)\int_z (\text{Re}(a_M(z))\text{Im}(F(z, t)) + \text{Im}(a_M(z))\text{Re}(F(z, t)))dz\bigg)dt$$

For each measurement of rank j, these equations may be rewritten as follows:

$$Q_j = \int_z \text{Re}(a_M(z))C_j(z)dz - \int_z \text{Im}(a_M(z))D_j(z)dz \quad \text{[Eq. 100]}$$

$$I_j = \int_z \text{Re}(a_M(z))E_j(z)dz - \int_z \text{Im}(a_M(z))F_j(z)dz \quad \text{[Eq. 101]}$$

with:

$$C_j(z) = \int_{T_{CAM}/4}^{T_{CAM}/2}(2\text{ Re}(A_R)\text{Re}(F_j(z,t)) + 2\text{ Im}(A_R)\text{Im}(F_j(z,t)))dt - \int_{3T_{CAM}/4}^{T_{CAM}}(2\text{ Re}(A_R)\text{Re}(F_j(z,t)) + 2\text{ Im}(A_R)\text{Im}(F_j(z,t)))dt \quad \text{[Eq. 102]}$$

$$D_j(z) = \int_{T_{CAM}/4}^{T_{CAM}/2}(2\text{ Re}(A_R)\text{Im}(F_j(z,t)) - 2\text{ Im}(A_R)\text{Re}(F_j(z,t)))dt - \int_{3T_{CAM}/4}^{T_{CAM}}(2\text{ Re}(A_R)\text{Im}(F_j(z,t)) - 2\text{ Im}(A_R)\text{Re}(F_j(z,t)))dt \quad \text{[Eq. 103]}$$

$$E_j(z) = \int_0^{T_{CAM}/4}(2\text{ Re}(A_R)\text{Re}(F_j(z,t)) + 2\text{ Im}(A_R)\text{Im}(F_j(z,t)))dt - \int_{T_{CAM}/2}^{3T_{CAM}/4}(2\text{ Re}(A_R)\text{Re}(F_j(z,t)) + 2\text{ Im}(A_R)\text{Im}(F_j(z,t)))dt \quad \text{[Eq. 104]}$$

$$F_j(z) = \int_0^{T_{CAM}/4}(2\text{ Re}(A_R)\text{Im}(F_j(z,t)) - 2\text{ Im}(A_R)\text{Re}(F_j(z,t)))dt - \int_{T_{CAM}/2}^{3T_{CAM}/4}(2\text{ Re}(A_R)\text{Im}(F_j(z,t)) - 2\text{ Im}(A_R)\text{Re}(F_j(z,t)))dt \quad \text{[Eq. 105]}$$

$$F_j(z,t) = e^{i(\omega_{CAM}t - \omega_0 z/v_L + \Phi_j(t - z/v_L) - \Omega_j(t-\delta))} \quad \text{[Eq. 106]}$$

One can also rewrite:

$$C_j(z) = 2\text{ Re}(A_R)(\int_{T_{CAM}/4}^{T_{CAM}/2}\text{Re}(F_j(z,t))dt - \int_{3T_{CAM}/4}^{T_{CAM}}\text{Re}(F_j(z,t))dt) + 2\text{ Im}(A_R)(\int_{T_{CAM}/4}^{T_{CAM}/2}\text{Im}(F_j(z,t))dt - \int_{3T_{CAM}/4}^{T_{CAM}}\text{Im}(F_j(z,t))dt \quad \text{[Eq. 107]}$$

$$D_j(z) = 2\text{ Re}(A_R)(\int_{T_{CAM}/4}^{T_{CAM}/2}\text{Im}(F_j(z,t))dt - \int_{3T_{CAM}/4}^{T_{CAM}}\text{Im}(F_j(z,t))dt) - 2\text{ Im}(A_R)(\int_{T_{CAM}/4}^{T_{CAM}/2}\text{Re}(F_j(z,t))dt - \int_{3T_{CAM}/4}^{T_{CAM}}\text{Re}(F_j(z,t))dt \quad \text{[Eq. 108]}$$

$$E_j(z) = 2\text{ Re}(A_R)(\int_0^{T_{CAM}/4}\text{Re}(F_j(z,t))dt - \int_{T_{CAM}/2}^{3T_{CAM}/4}\text{Re}(F_j(z,t))dt) + 2\text{ Im}(A_R)(\int_0^{T_{CAM}/4}\text{Im}(F_j(z,t))dt - \int_{T_{CAM}/2}^{3T_{CAM}/4}\text{Im}(F_j(z,t))dt \quad \text{[Eq. 109]}$$

$$F_j(z) = 2\text{ Re}(A_R)(\int_0^{T_{CAM}/4}\text{Im}(F_j(z,t))dt - \int_{T_{CAM}/2}^{3T_{CAM}/4}\text{Im}(F_j(z,t))dt) - 2\text{ Im}(A_R)(\int_0^{T_{CAM}/4}\text{Re}(F_j(z,t))dt - \int_{T_{CAM}/2}^{3T_{CAM}/4}\text{Re}(F_j(z,t))dt \quad \text{[Eq. 110]}$$

The following notations are used:

$$H_{13\ Re\ j}(z) = \int_0^{T_{CAM}/4}\text{Re}(F_j(z,t))dt - \int_{T_{CAM}/2}^{3T_{CAM}/4}\text{Re}(F_j(z,t))dt \quad \text{[Eq. 111]}$$

$$H_{13\ Im\ j}(z) = \int_0^{T_{CAM}/4}\text{Im}(F_j(z,t))dt - \int_{T_{CAM}/2}^{3T_{CAM}/4}\text{Im}(F_j(z,t))dt \quad \text{[Eq. 112]}$$

$$H_{24\ Re\ j}(z) = \int_{T_{CAM}/4}^{T_{CAM}/2}\text{Re}(F_j(z,t))dt - \int_{3T_{CAM}/4}^{T_{CAM}}\text{Re}(F_j(z,t))dt \quad \text{[Eq. 113]}$$

$$H_{24\ Im\ j}(z) = \int_{T_{CAM}/4}^{T_{CAM}/2}\text{Im}(F_j(z,t))dt - \int_{3T_{CAM}/4}^{T_{CAM}}\text{Im}(F_j(z,t))dt \quad \text{[Eq. 114]}$$

One can then rewrite:

$$C_j(z) = 2\text{ Re}(A_R)H_{24\ Re\ j}(z) + 2\text{ Im}(A_R)H_{24\ Im\ j}(z) \quad \text{[Eq. 115]}$$

$$D_j(z) = 2\text{ Re}(A_R)H_{24\ Im\ j}(z) - 2\text{ Im}(A_R)H_{24\ Re\ j}(z) \quad \text{[Eq. 116]}$$

$$E_j(z) = 2\text{ Re}(A_R)H_{13\ Re\ j}(z) + 2\text{ Im}(A_R)H_{13\ Im\ j}(z) \quad \text{[Eq. 117]}$$

$$F_j(z) = 2\text{ Re}(A_R)H_{13\ Im\ j}(z) - 2\text{ Im}(A_R)H_{13\ Re\ j}(z) \quad \text{[Eq. 118]}$$

Each of the M obtained measurements may, as previously, be rewritten in form $Y_j = I_j + iQ_j$, with:

$$Q_j = \sum_{k=1}^L \left(\text{Re}(a_M(k \cdot \Delta z))\int_{(k-1)\cdot\Delta z}^{k\cdot\Delta z} C_j(z)dz - \text{Im}(a_M(k \cdot \Delta z))\int_{(k-1)\cdot\Delta z}^{k\cdot\Delta z} D_j(z)dz\right) \quad \text{[Eq. 119]}$$

$$I_j = \sum_{k=1}^L \left(\text{Re}(a_M(k \cdot \Delta z))\int_{(k-1)\cdot\Delta z}^{k\cdot\Delta z} E_j(z)dz - \text{Im}(a_M(k \cdot \Delta z))\int_{(k-1)\cdot\Delta z}^{k\cdot\Delta z} F_j(z)dz\right) \quad \text{[Eq. 120]}$$

In this example, pitch $\Delta z$ will preferably be selected to be much smaller than wavelength $\lambda_L$ with $\lambda_L\ (3*10^8)*2\pi/\omega_0$.

Considering a reference absorption profile $a_{Mref}$ along the light propagation path, one has:

$$Q_{j\ Ref} = \sum_{k=1}^L \left(\text{Re}(a_{M\ Ref}(k \cdot \Delta z))\int_{(k-1)\cdot\Delta z}^{k\cdot\Delta z} C_j(z)dz - \text{Im}(a_{M\ Ref}(k \cdot \Delta z))\int_{(k-1)\cdot\Delta z}^{k\cdot\Delta z} D_j(z)dz\right) \quad \text{[Eq. 121]}$$

$$I_{j\ Ref} = \sum_{k=1}^L \left(\text{Re}(a_{M\ Ref}(k \cdot \Delta z))\int_{(k-1)\cdot\Delta z}^{k\cdot\Delta z} E_j(z)dz - \text{Im}(a_{M\ Ref}(k \cdot \Delta z))\int_{(k-1)\cdot\Delta z}^{k\cdot\Delta z} F_j(z)dz\right) \quad \text{[Eq. 122]}$$

that is:

$$Y_{j\ Ref} = \sum_{k=1}^L \left(\text{Re}(a_{M\ Ref}(k \cdot \Delta z))\int_{(k-1)\cdot\Delta z}^{k\cdot\Delta z} E_j(z)dz - \right. \quad \text{[Eq. 123]}$$

-continued $$Y_{j\,Ref} = \sum_{k=1}^{L}\left(\text{Re}(a_{M\,Ref}(k\cdot\Delta z))\int_{(k-1)\Delta z}^{k\cdot\Delta z} E_j(z)dz - \right.$$
$$\text{Im}(a_{M\,Ref}(k\cdot\Delta z))\int_{(k-1)\Delta z}^{k\cdot\Delta z} F_j(z)dz + i\left(\text{Re}(a_{M\,Ref}(k\cdot\Delta z))\right.$$
$$\left.\left.\int_{(k-1)\Delta z}^{k\cdot\Delta z} C_j(z)dz - \text{Im}(a_{M\,Ref}(k\cdot\Delta z))\int_{(k-1)\Delta z}^{k\cdot\Delta z} D_j(z)dz\right)\right) \quad [\text{Eq. 124}]$$

$$Y_{j\,Ref} = \sum_{k=1}^{L}\left(\text{Re}(a_{M\,Ref}(k\cdot\Delta z))\int_{(k-1)\Delta z}^{k\cdot\Delta z} (E_j(z)+iC_j(z))dz - \right.$$
$$\left.\text{Im}(a_{M\,Ref}(k\cdot\Delta z))\int_{(k-1)\Delta z}^{k\cdot\Delta z} (F_j(z)+iD_j(z))dz\right) \quad [\text{Eq. 125}]$$

$$Y_{j\,Ref} = \quad [\text{Eq. 126}]$$
$$\sum_{k=1}^{L}\Big(\text{Re}(a_{M\,Ref}(k\cdot\Delta z))\int_{(k-1)\Delta z}^{k\cdot\Delta z}(2\text{Re}(A_R)H_{13\,Re\,j}(z)+2\text{Im}(A_R)$$
$$H_{13\,Im\,j}(z)+i(2\text{Re}(A_R)H_{24\,Re\,j}(z)+2\text{Im}(A_R)H_{24\,Im\,j}(z)))dz - $$
$$\text{Im}(a_{M\,Ref}(k\cdot\Delta z))\int_{(k-1)\Delta z}^{k\cdot\Delta z}(2\text{Re}(A_R)H_{13\,Im\,j}(z) - $$
$$2\text{Im}(A_R)H_{13\,Re\,j}(z)+i(2\text{Re}(A_R)H_{24\,Im\,j}(z)-2\text{Im}(A_R)H_{24\,Re\,j}(z)))dz\Big)$$

$$Y_{j\,Ref} = \sum_{k=1}^{L}\Big(2\text{Re}(a_{M\,Ref}(k\cdot\Delta z)) \quad [\text{Eq. 127}]$$
$$\text{Re}(A_R)\int_{(k-1)\Delta z}^{k\cdot\Delta z}(H_{13\,Re\,j}(z)+iH_{24\,Re\,j}(z))dz + $$
$$2\text{Re}(a_{M\,Ref}(k\cdot\Delta z))\text{Im}(A_R)\int_{(k-1)\Delta z}^{k\cdot\Delta z}(H_{13\,Im\,j}(z)+iH_{24\,Im\,j}(z))dz - $$
$$2\text{Im}(a_{M\,Ref}(k\cdot\Delta z))\text{Re}(A_R)\int_{(k-1)\Delta z}^{k\cdot\Delta z}(H_{13\,Im\,j}(z)+iH_{24\,Im\,j}(z))dz + $$
$$2\text{Im}(a_{M\,Ref}(k\cdot\Delta z))\text{Im}(A_R)\int_{(k-1)\Delta z}^{k\cdot\Delta z}(H_{13\,Ref\,j}(z)+iH_{24\,Re\,j}(z))dz\Big)$$

$$Y_{j\,Ref} = 2 \quad [\text{Eq. 128}]$$
$$\sum_{k=1}^{L}\Big(\text{Re}(a_{M\,Ref}(k\cdot\Delta z))\Big(\text{Re}(A_R)\int_{(k-1)\Delta z}^{k\cdot\Delta z}(H_{13\,Re\,j}(z)+iH_{24\,Re\,j}(z))dz + $$
$$\text{Im}(A_R)\int_{(k-1)\Delta z}^{k\cdot\Delta z}(H_{13\,Im\,j}(z)+iH_{24\,Im\,j}(z))dz - $$
$$\text{Im}(a_{M\,Ref}(k\cdot\Delta z))\text{Re}(A_R)\int_{(k-1)\Delta z}^{k\cdot\Delta z}(H_{13\,Im\,j}(z)+iH_{24\,Im\,j}(z))dz - $$
$$\text{Im}(A_R)\int_{(k-1)\Delta z}^{k\cdot\Delta z}(H_{13\,Ref\,j}(z)+iH_{24\,Re\,j}(z))dz\Big)\Big)$$

Having identified the relation between the measurements and the absorption profile according to equal to equation 128, the following matrix relation can be established:

$$Y_j = \mathcal{A}_{Re\,j,k}\text{Re}(a_M) - \mathcal{A}_{Im\,j,k}\text{Im}(a_M) \quad [\text{Eq. 129}]$$

where $A_{Re}$ and $A_{Im}$ are two matrices each having M rows and L columns, and $a_M$ is a vector of L rows and one column.

With:

$$\mathcal{A}_{Re\,j,k} = 2(\text{Re}(A_R)\int_{(k-1)\Delta z}^{k\cdot\Delta z}(H_{13\,Re\,j}(z)+iH_{24\,Re\,j}(z))$$
$$dz + \text{Im}(A_R)\int_{(k-1)\Delta z}^{k\cdot\Delta z}(H_{13\,Im\,j}(z)+iH_{24\,Im\,j}(z))dz) \quad [\text{Eq. 130}]$$

$$\mathcal{A}_{Im\,j,k} = 2(\text{Re}(A_R)\int_{(k-1)\Delta z}^{k\cdot\Delta z}(H_{13\,Im\,j}(z)+iH_{24\,Im\,j}(z))$$
$$dz - \text{Im}(A_R)\int_{(k-1)\Delta z}^{k\cdot\Delta z}(H_{13\,Re\,j}(z)+iH_{24\,Re\,j}(z))dz) \quad [\text{Eq. 131}]$$

The same method of reconstruction of absorption profile $a_M$ as in the previous examples (equation 42) can then be used.

It should be noted that the embodiment of FIG. 5 may also be adapted for applications of depth measurement in a scene. In this case, the assembly will be similar to that of FIG. 7, but with a single acoustic modulator MAO1, placed on the object arm, enabling to apply modulation sequence Φ, and by replacing the low-frequency sensor 609 of FIG. 6 with a synchronous sensor 109 of the type described in relation with FIG. 5, enabling to apply demodulation sequence Q in the electronic field.

Figures 8, 9:
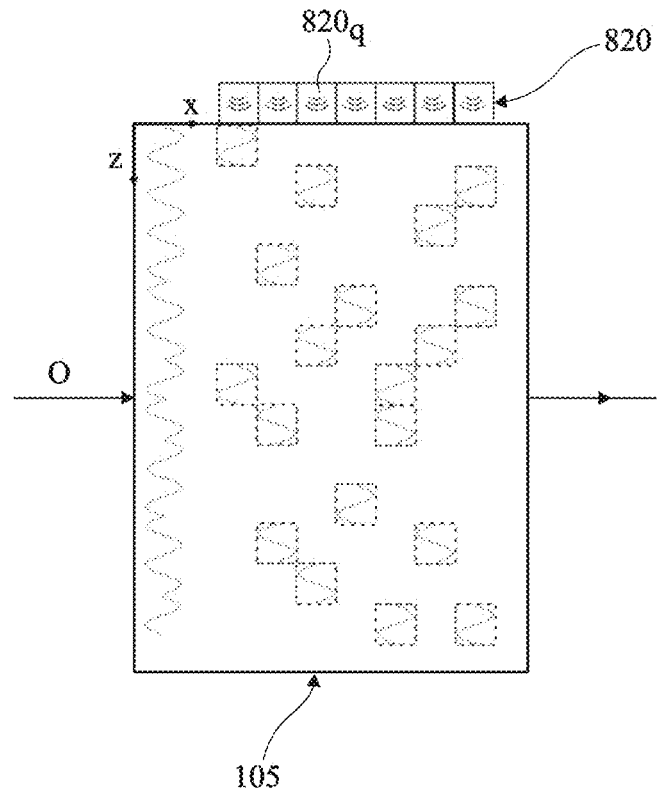
FIG. 8 illustrates the operation of an alternative embodiment of an acoustic-optical imaging system.
FIG. 9 illustrates in further detail the operation of the variant of FIG. 8.

FIG. 8 illustrates the operation of an alternative embodiment of the acoustic-optical imaging system of FIG. 5.

In the example of FIG. 5, a system of acquisition of a one-dimension absorption profile $a_M$ has been provided. For this purpose, a single ultrasound transducer (or a single group of simultaneously controlled ultrasound transducers) 120 (FIG. 5) applies a marking sine wave ballistically propagating in a local area of the sample, for example, a column-shaped area. The propagation direction of the marking acoustic wave corresponds to the direction of reconstruction of absorption profile $a_M$ (direction z in the above-detailed formulas).

In the variant of FIG. 8, it is provided to extend the measurement principle detailed in relation with FIG. 5 to the reconstruction of a two-dimensional absorption profile, x and z, for example, orthogonal.

For this purpose, a reference acoustic excitation wave exhibiting phase jumps defined according to a random or pseudo-random pattern Φ is used as previously. This wave is emitted not longer by means of a single transducer according to a single trajectory, but by means of a linear array 820 of W elementary transducers $820_q$ spatially distributed along axis x, W being an integer greater than or equal to 2 and q being an integer in the range from 1 to W. In this example, the W transducers $820_q$ are aligned along axis x, and each transducer $820_q$ is arranged to emit along a main propagation direction parallel to axis z.

In the variant of FIG. 8, the acoustic excitation wave is emitted in fractions by the different transducers in random or pseudo-random fashion, according to a function γ. Each wave fraction emitted by a transducer preferably corresponds to a single period $T_{US}$ or to an integral number of periods $T_{US}$ of the acoustic excitation wave. A same fraction of the acoustic excitation wave may be simultaneously emitted by a plurality of transducers $820_q$ (that is, simultaneously from a plurality of positions x).

The measurement principle can then be described by means of the following equations, by using the previously-used formalism. The pitch between transducers is designated hereafter by Δx and $\gamma_x$ designates a random or pseudo-random binary sequence enabling to model the activation of the transducer located at position x over time. Term $a_x(z)$ is a column vector of L values representing the absorption profile along z at position x.

The wave of the reference beam and the wave of the object beam can be written as:

$$E_r(t)A_R e^{i\omega_L t} \quad \text{[Eq. 132]}$$

$$E_{s,j}(t) = \quad \text{[Eq. 133]}$$

$$A_D e^{i\omega_L t} + \sum_{q=1}^{W} \left( \int_z a_{q\Delta x}(z) Y_{q\Delta x,j}(t-z/\upsilon_{US}) e^{i\left(\omega_L t + \omega_{US}(t-z/\upsilon_{US}) + \pi\Phi_j(t-z/\upsilon_{US})\right)} dz + \int_z a_{q\Delta x}(z) Y_{q\Delta x,j}(t-z/\upsilon_{US}) e^{i\left(\omega_L t - \omega_{US}(t-z/\upsilon_{US}) - \pi\Phi_j(t-z/\upsilon_{US})\right)} dz \right)$$

The interference $s_j(t)$ measured at the level of the sensor corresponding to a measurement of rank j can then be written as:

$$s_j(t) = |E_r(t) + E_{s,j}(t)|^2 \quad \text{[Eq. 134]}$$

$$s_j(t) = \quad \text{[Eq. 135]}$$

$$\left| A_R e^{i\omega_L t} + A_D e^{i\omega_L t} + \sum_{q=1}^{W} \left( \int_z a_{q\Delta x}(z) Y_{q\Delta x,j}(t-z/\upsilon_{US}) e^{i\left(\omega_L t + \omega_{US}(t-z/\upsilon_{US}) + \pi\Phi_j(t-z/\upsilon_{US})\right)} dz + \int_z a_{q\Delta x}(z) Y_{q\Delta x,j}(t-z/\upsilon_{US}) e^{i\left(\omega_L t - \omega_{US}(t-z/\upsilon_{US}) - \pi\Phi_j(t-z/\upsilon_{US})\right)} dz \right) \right|^2$$

$$s_j(t) = |e^{i\omega_L t}|^2 \left| A_R + A_D + \sum_{q=1}^{W} \left( \int_z a_{q\Delta x}(z) Y_{q\Delta x,j}(t-z/\upsilon_{US}) e^{i(\omega_{US}(t-z/\upsilon_{US}) + \pi\Phi_j(t-z/\upsilon_{US}))} dz + \int_z a_{q\Delta x}(z) Y_{q\Delta x,j}(t-z/\upsilon_{US}) e^{i(-\omega_{US}(t-z/\upsilon_{US}) - \pi\Phi_j(t-z/\upsilon_{US}))} dz \right) \right|^2 \quad \text{[Eq. 136]}$$

$$s_j(t) = \left| A_R + A_D + 2\sum_{q=1}^{W} \left( \int_z a_{q\Delta x}(z) Y_{q\Delta x,j}(t-z/\upsilon_{US}) \cos(\omega_{US}(t-z/\upsilon_{US}) + \pi\Phi_j(t-z/\upsilon_{US})) dz \right) \right|^2 \quad \text{[Eq. 137]}$$

Four phases are measured by demodulation at the sensor level:

$$I_j = \sum_{p=1}^{N} \Pi_j(p) \left( \int_{pT_{US}}^{pT_{US}+T_{US}/4} s_j(t) dt - \int_{pT_{US}+T_{US}/2}^{pT_{US}+3T_{US}/4} s_j(t) dt \right) \quad \text{[Eq. 138]}$$

$$Q_j = \sum_{p=1}^{N} \Pi_j(p) \left( \int_{pT_{US}+T_{US}/4}^{pT_{US}+T_{US}/2} s_j(t) dt - \int_{pT_{US}+3T_{US}/4}^{pT_{US}+T_{US}} s_j(t) dt \right) \quad \text{[Eq. 139]}$$

with:

$$\Pi_j(p) = 2\left(\Omega_j(p) - \frac{1}{2}\right) \quad \text{[Eq. 140]}$$

whereby, for example, for path Q:

$$Q_j = \sum_{p=1}^{N} \Pi_j(p) \quad \text{[Eq. 141]}$$

$$\left\{ \int_{pT_{US}+T_{US}/4}^{pT_{US}+T_{US}/2} \left( \text{Re}\left( 2\sum_{q=1}^{W} \left( \int_z a_{q\Delta x}(z) Y_{q\Delta x,j}(t-z/\upsilon_{US}) \begin{array}{c} A_D + A_R + \\ \cos(\omega_{US}(t-z/\upsilon_{US}) + \\ \pi\Phi_j(t-z/\upsilon_{US})) dz \end{array} \right) \right) \right)^2 dt - \right.$$

$$\int_{pT_{US}+3T_{US}/4}^{pT_{US}+T_{US}} \left( \text{Re}\left( 2\sum_{q=1}^{W} \left( \int_z a_{q\Delta x}(z) Y_{q\Delta x,j}(t-z/\upsilon_{US}) \begin{array}{c} A_D + A_R + \\ \cos(\omega_{US}(t-z/\upsilon_{US}) + \\ \pi\Phi_j(t-z/\upsilon_{US})) dz \end{array} \right) \right) \right)^2 dt +$$

$$\left. \int_{pT_{US}+T_{US}/4}^{pT_{US}+T_{US}/2} \left( \text{Im}\left( 2\sum_{q=1}^{W} \left( \int_z a_{q\Delta x}(z) Y_{q\Delta x,j}(t-z/\upsilon_{US}) \begin{array}{c} A_D + A_R + \\ \cos(\omega_{US}(t-z/\upsilon_{US}) + \\ \pi\Phi_j(t-z/\upsilon_{US})) dz \end{array} \right) \right) \right)^2 dt \right\}$$

The terms which do not comprise the component $A_R$ of the reference arm are neglected and the following term is defined:

$$G(t,z) = \cos(\omega_{US}(t-z/\upsilon_{US}) + \pi\Phi_j(t-z/\upsilon_{US})) \quad \text{[Eq. 142]}$$

Equation 141 is then simplified as follows:

$$Q_j = \sum_{p=1}^{N} \Pi_j(p) \left( \int_{pT_{US}+T_{US}/4}^{pT_{US}+T_{US}/2} 4\text{Re}(A_R) \quad \text{[Eq. 143]} \right.$$

$$\left( \sum_{q=1}^{W} \left( \int_z \text{Re}(a_{q\Delta x}(z) Y_{q\Delta x,j}(t-z/\upsilon_{US})(G_j(t,z))) dz \right) \right) dt -$$

$$\int_{pT_{US}+3T_{US}/4}^{pT_{US}+T_{US}} 4\text{Re}(A_R) \left( \sum_{q=1}^{W} \left( \int_z \text{Re}(a_{q\Delta x}(z) Y_{q\Delta x,j}(t-z/\upsilon_{US}) G_j(t,z)) \right) \right.$$

$$\left. dz \right) dt + \int_{pT_{US}+T_{US}/4}^{pT_{US}+T_{US}/2} 4\text{Im}(A_R) \left( \sum_{q=1}^{W} \left( \int_z \text{Im}( \right. \right.$$

$$\left. \left. a_{q\Delta x}(z) Y_{q\Delta x,j}(t-z/\upsilon_{US}) G_j(t,z)) dz \right) \right) dt - \int_{pT_{US}+3T_{US}/4}^{pT_{US}+T_{US}} 4$$

$$\left. \text{Im}(A_R) \left( \sum_{q=1}^{W} \left( \int_z \text{Im}(q_{q\Delta x}(z) Y_{q\Delta x,j}(t-z/\upsilon_{US}) G_j(t,z)) dz \right) \right) dt \right)$$

One then has:

$$Q_j = \sum_{p=1}^{N} \Pi_j(p) \left( \int_{pT_{US}+T_{US}/4}^{pT_{US}+T_{US}/2} 4\text{Re}(A_R) \quad \text{[Eq. 144]} \right.$$

$$\left( \sum_{q=1}^{W} \left( \int_z \text{Re}(a_{q\Delta x}(z) Y_{q\Delta x,j}(t-z/\upsilon_{US})) \text{Re}(G_j(t,z)) dz \right) \right)$$

$$dt - \int_{pT_{US}+3T_{US}/4}^{pT_{US}+T_{US}} 4\text{Re}(A_R)$$

$$\left( \sum_{q=1}^{W} \left( \int_z \text{Re}(a_{q\Delta x}(z) Y_{q\Delta x,j}(t-z/\upsilon_{US})) \text{Re}(G_j(t,z)) dz \right) \right) dt +$$

$$\int_{pT_{US}+T_{US}/4}^{pT_{US}+T_{US}/2} 4\mathrm{Im}(A_R) \left( \sum_{q=1}^{W} \left( \int_z \mathrm{Im}(a_{q\Delta x}(z)) \right. \right.$$

$$Y_{q\Delta x,j}(t-z/\upsilon_{US})) \mathrm{Re}(G_j(t,z))dz) dt - \int_{pT_{US}+3T_{US}/4}^{pT_{US}+T_{US}} 4\mathrm{Im}(A_R)$$

$$\left( \sum_{q=1}^{W} \left( \int_z \mathrm{Im}(a_{q\Delta x}(z)) Y_{q\Delta x,j}(t-z/\upsilon_{US})) \mathrm{Re}(G_j(t,z)) \right) \right) dt$$

$$Q_j = \sum_{q=1}^{W} \left( \int_z \mathrm{Re}(a_{q\Delta x}(z)) \right) \left( 4\mathrm{Re}(A_R) \right.$$  [Eq. 145]

$$\left( \sum_{p=1}^{N} \Pi_j(p) \left( \int_{pT_{US}+T_{US}/4}^{pT_{US}+T_{US}/2} Y_{q\Delta x,j}(t-z/\upsilon_{US}) \mathrm{Re}(G_j(t,z))dt - \right. \right.$$

$$\left. \int_{pT_{US}+3T_{US}/4}^{pT_{US}+T_{US}} Y_{q\Delta x,j}(t-z/\upsilon_{US}) \mathrm{Re}(G_j(t,z))dt \right) \right) dz + \int_z \mathrm{Im}(a_{q\Delta x}(z))$$

$$\left( 4\mathrm{Im}(A_R) \left( \sum_{p=1}^{N} \Pi_j(p) \left( \int_{pT_{US}+T_{US}/4}^{pT_{US}+T_{US}/2} Y_{q\Delta x,j}(t-z/\upsilon_{US}) \mathrm{Re}(G_j(t,z)) \right. \right. \right.$$

$$\left. \left. \left. dt - \int_{pT_{US}+3T_{US}/4}^{pT_{US}+T_{US}} Y_{q\Delta x,j}(t-z/\upsilon_{US}) \mathrm{Re}(G_j(t,z))dt \right) \right) \right) dz$$

Similarly, it can be shown that:

$$I_j = \sum_{q=1}^{W} \left( \int_z \mathrm{Re}(a_{q\Delta x}(z)) \right)$$ [Eq. 146]

$$\left( 4\mathrm{Re}(A_R) \left( \sum_{p=1}^{N} \Pi_j(p) \left( \int_{pT_{US}}^{pT_{US}+T_{US}/4} Y_{q\Delta x,j}(t-z/\upsilon_{US}) \mathrm{Re}(G_j(t,z)) \right. \right. \right.$$

$$\left. \left. dt - \int_{pT_{US}+T_{US}/2}^{pT_{US}+3T_{US}/4} Y_{q\Delta x,j}(t-z/\upsilon_{US}) \mathrm{Re}(G_j(t,z))dt \right) \right) dz + \int_z \mathrm{Im}($$

$$a_{q\Delta x}(z) \left( 4\mathrm{Im}(A_R) \left( \sum_{p=1}^{N} \Pi_j(p) \left( \int_{pT_{US}}^{pT_{US}+T_{US}/4} Y_{q\Delta x,j}(t-z/\upsilon_{US}) \mathrm{Re}(\right. \right. \right.$$

$$\left. \left. \left. G_j(t,z))dt - \int_{pT_{US}+T_{US}/2}^{pT_{US}+3T_{US}/4} Y_{q\Delta x,j}(t-z/\upsilon_{US}) \mathrm{Re}(G_j(t,z))dt \right) \right) \right) dz$$

For each of the M measurements of the phase of acquisition of absorption profile $a_M$, the following can be written:

$$Q_j = \sum_{q=1}^{W} \left( \int_z \mathrm{Re}(a_{q\Delta x}(z)) C_{jq}(z) dz + \int_z \mathrm{Im}(a_{q\Delta x}(z)) D_{jq}(z) dz \right)$$ [Eq. 147]

$$I_j = \sum_{q=1}^{W} \left( \int_z \mathrm{Re}(a_{q\Delta x}(z)) E_{jq}(z) dz + \int_z \mathrm{Im}(a_{q\Delta x}(z)) F_{jq}(z) dz \right)$$ [Eq. 148]

with:

$$C_{jq}(z) = 4\mathrm{Re}(A_R)$$ [Eq. 149]

$$\sum_{p=1}^{N} \Pi_j(p) \left( \int_{pT_{US}+T_{US}/4}^{pT_{US}+T_{US}/2} Y_{q\Delta x,j}(t-z/\upsilon_{US})\cos(\omega_{US}(t-z/\upsilon_{US}) + \right.$$

$$\left. \pi\Phi_j(t-z/\upsilon_{US}))dt - \int_{pT_{US}+3T_{US}/4}^{pT_{US}+T_{US}} Y_{q\Delta x,j}(t-z/\upsilon_{US}) \right.$$

$$\left. \cos(\omega_{US}(t-z/\upsilon_{US}) + \pi\Phi_j(t-z/\upsilon_{US}))dt \right)$$

[Eq. 150]

$$D_{jq}(z) = 4\mathrm{Im}(A_R)$$

$$\sum_{p=1}^{N} \Pi_j(p) \left( \int_{pT_{US}+T_{US}/4}^{pT_{US}+T_{US}/2} Y_{q\Delta x,j}(t-z/\upsilon_{US})\cos(\omega_{US}(t-z/\upsilon_{US}) + \right.$$

$$\left. \pi\Phi_j(t-z/\upsilon_{US}))dt - \int_{pT_{US}+3T_{US}/4}^{pT_{US}+T_{US}} Y_{q\Delta x,j}(t-z/\upsilon_{US}) \right.$$

$$\left. \cos(\omega_{US}(t-z/\upsilon_{US}) + \pi\Phi_j(t-z/\upsilon_{US}))dt \right)$$

[Eq. 151]

$$E_{jq}(z) = 4\mathrm{Re}(A_R)$$

$$\sum_{p=1}^{N} \Pi_j(p) \left( \int_{pT_{US}}^{pT_{US}+T_{US}/4} Y_{q\Delta x,j}(t-z/\upsilon_{US})\cos(\omega_{US}(t-z/\upsilon_{US}) + \right.$$

$$\left. \pi\Phi_j(t-z/\upsilon_{US}))dt - \int_{pT_{US}+T_{US}/2}^{pT_{US}+3T_{US}/4} Y_{q\Delta x,j}(t-z/\upsilon_{US}) \right.$$

$$\left. \cos(\omega_{US}(t-z/\upsilon_{US}) + \pi\Phi_j(t-z/\upsilon_{US}))dt \right)$$

[Eq. 152]

$$F_{jq}(z) = 4\mathrm{Im}(A_R)$$

$$\sum_{p=1}^{N} \Pi_j(p) \left( \int_{pT_{US}}^{pT_{US}+T_{US}/4} Y_{q\Delta x,j}(t-z/\upsilon_{US})\cos(\omega_{US}(t-z/\upsilon_{US}) + \right.$$

$$\left. \pi\Phi_j(t-z/\upsilon_{US}))dt - \int_{pT_{US}+T_{US}/2}^{pT_{US}+3T_{US}/4} Y_{q\Delta x,j}(t-z/\upsilon_{US}) \right.$$

$$\left. \cos(\omega_{US}(t-z/\upsilon_{US}) + \pi\Phi_j(t-z/\upsilon_{US}))dt \right)$$

Each measurement can be rewritten in form $Y_j = I_j + iQ_j$, with:

$$Q_j = \sum_{q=1}^{W} \sum_{k=1}^{L} \left( \mathrm{Re}(a_{q\Delta x}(k\Delta z)) \int_{(k-1)\Delta z}^{k\Delta z} C_{jq}(z) dz + \right.$$ [Eq. 153]

$$\left. \mathrm{Im}(a_{q\Delta x}(k\Delta z)) \int_{(k-1)\Delta z}^{k\Delta z} D_{jq}(z) dz \right)$$

$$I_j = \sum_{q=1}^{W} \sum_{k=1}^{L} \left( \mathrm{Re}(a_{q\Delta x}(k\Delta z)) \int_{(k-1)\Delta z}^{k\Delta z} E_{jq}(z) dz + \right.$$ [Eq. 154]

$$\left. \mathrm{Im}(a_{q\Delta x}(k\Delta z)) \int_{(k-1)\Delta z}^{k\Delta z} F_{jq}(z) dz \right)$$

Term $\Delta z$ here represents a fraction of the wavelength $\lambda_{US} = T_{US} * \upsilon_{US}$ of the ultrasound excitation signal of pulse $\omega_{US}$, selected to be able to consider the absorption as being constant over an interval $\Delta z$. According to the notation used, the considered medium has a thickness $L * \Delta z$.

To construct the transition matrix of the system, terms I and Q are rewritten as follows, considering a contribution of reference $a_{refx}(z)$ of each position x of the acoustic marking area, for example, enabling to model the acoustic marking efficiency at each position of the marking area:

$$Q_{jRef} = \sum_{q=1}^{W}\sum_{k=1}^{L}\left(\text{Re}(a_{Ref\,q\Delta x}(k\Delta z))\int_{(k-1)\Delta z}^{k\Delta z} C_{jq}(z)dz + \right.$$

[Eq. 155]

$$\left. \text{Im}(a_{Ref\,q\Delta x}(k\Delta z))\int_{(k-1)\Delta z}^{k\Delta z} D_{jq}(z)dz\right)$$

$$I_{jRef} = \sum_{q=1}^{W}\sum_{k=1}^{L}\left(\text{Re}(a_{Ref\,q\Delta x}(k\Delta z))\int_{(k-1)\Delta z}^{k\Delta z} E_{jq}(z)dz + \right.$$

[Eq. 156]

$$\left. \text{Im}(a_{Ref\,q\Delta x}(k\Delta z))\int_{(k-1)\Delta z}^{k\Delta z} F_{jq}(z)dz\right)$$

whereby:

$$Y_{jRef} =$$ [Eq. 157]

$$\sum_{q=1}^{W}\sum_{k=1}^{L}\left(\left(\text{Re}(a_{Ref\,q\Delta x}(k\Delta z))\int_{(k-1)\Delta z}^{k\Delta z} E_{jq}(z)dz + \text{Im}(a_{Ref\,q\Delta x}(k\Delta z))\right.\right.$$

$$\left.\int_{(k-1)\Delta z}^{k\Delta z} F_{jq}(z)dz\right) + i\left(\text{Re}(a_{Ref\,q\Delta x}(k\Delta z))\int_{(k-1)\Delta z}^{k\Delta z} C_{jq}(z)dz +$$

$$\left.\left.\text{Im}(a_{Ref\,q\Delta x}(k\Delta z))\int_{(k-1)\Delta z}^{k\Delta z} D_{jq}(z)dz\right)\right)$$

$$Y_{jRef} =$$ [Eq. 158]

$$\sum_{q=1}^{W}\sum_{k=1}^{L}\left(4\text{Re}(A_R)\text{Re}(a_{Ref\,q\Delta x}(k\Delta z))\int_{(k-1)\Delta z}^{k\Delta z}(S13_{jq}(z)+iS24_{jq}(z))dz + \right.$$

$$\left. 4\text{Im}(A_R)\text{Im}(a_{Ref\,q\Delta x}(k\Delta z))\int_{(k-1)\Delta z}^{k\Delta z}(S13_{jq}(z)+iS24_{jq}(z))dz\right)$$

with:

$$S13_{jq}(z) =$$ [Eq. 159]

$$\sum_{p=1}^{N}\Pi_j(p)\left(\int_{pT_{US}}^{pT_{US}+T_{US}/4} Y_{q\Delta x,j}(t-z/v_{US})\cos(\omega_{US}(t-z/v_{US}) + \right.$$

$$\pi\Phi_j(t-z/v_{US}))dt - \int_{pT_{US}+T_{US}/2}^{pT_{US}+3T_{US}/4} Y_{q\Delta x,j}(t-z/v_{US})$$

$$\left. \cos(\omega_{US}(t-z/v_{US})+\pi\Phi_j(t-z/v_{US}))dt\right)$$

$$S24_{jq}(z) =$$ [Eq. 160]

$$\sum_{p=1}^{N}\Pi_j(p)\left(\int_{pT_{US}+T_{US}/4}^{pT_{US}+T_{US}/2} Y_{q\Delta x,j}(t-z/v_{US})\cos(\omega_{US}(t-z/v_{US}) + \right.$$

$$\pi\Phi_j(t-z/v_{US}))dt - \int_{pT_{US}+3T_{US}/4}^{pT_{US}+T_{US}} Y_{q\Delta x,j}(t-z/v_{US})$$

$$\left. \cos(\omega_{US}(t-z/v_{US})+\pi\Phi_j(t-z/v_{US}))dt\right)$$

that is:

$$Y_{jRef} = \sum_{q=1}^{W}\sum_{k=1}^{L}\left(\left(4\text{Re}(A_R)\text{Re}(a_{Ref\,q\Delta x}(k\Delta z)) + \right.\right.$$ [Eq. 161]

$$\left. 4\text{Im}(A_R)\text{Im}(a_{Ref\,q\Delta x}(k\Delta z))\int_{(k-1)\Delta z}^{k\Delta z}(S13_{jq}(z)+iS24_{jq}(z))dz\right)$$

Having identified the relation between the measurements and the absorption profile according to equal to equation 161, the following matrix relation can be established:

$$Y_j = \mathcal{A}_{Re}\text{Re}(a_{xz}) + \mathcal{A}_{Im}\text{Im}(a_{xz})$$ [Eq. 162]

where $a_{xz}$ is a vector of L*W rows and one column corresponding to the concatenation of the W absorption profiles of L points each, respectively corresponding to the W measurement positions on axis x, such that:

$$a_{xz}=(a_{\Delta x}(\Delta z),\ldots,a_{\Delta x}(L\Delta z),a_{2\Delta x}(\Delta z),\ldots,$$
$$a_{2\Delta x}(L\Delta z),\ldots,a_{W\Delta x}(\Delta z),\ldots,a_{W\Delta x}(L\Delta z))^T$$ [Eq. 163]

and where $A_{Re}$ and $A_{Im}$ are two matrices of M rows and L*W columns, each, such that:

$$\mathcal{A}_{Re}=(\mathcal{A}_{Re\,j,1,1},\ldots,\mathcal{A}_{Re\,j,1,L},\mathcal{A}_{Re\,j,2,1},\ldots,$$
$$\mathcal{A}_{Re\,j,2,L},\mathcal{A}_{Re\,j,W,1},\ldots,\mathcal{A}_{Re\,j,W,L})$$ [Eq. 164]

$$\mathcal{A}_{Im}=(\mathcal{A}_{Im\,j,1,1},\ldots,\mathcal{A}_{Im\,j,1,L},\mathcal{A}_{Im\,j,2,1},\ldots,$$
$$\mathcal{A}_{Im\,j,2,L},\mathcal{A}_{Im\,j,W,1},\ldots,\mathcal{A}_{Im\,j,W,L}$$ [Eq. 165]

$$\mathcal{A}_{Re\,j,\Delta,k}=4\,\text{Re}(A_R)\text{Re}(a_{Ref\,q\Delta x}(k\Delta z))\int_{(k-1)\Delta z}^{k\Delta z}$$
$$(s13_{jq}(z)+is24_{jq}(z))dz$$ [Eq. 166]

$$\mathcal{A}_{Re\,j,\Delta,k}=4\,\text{Im}(A_R)\text{Im}(a_{Ref\,q\Delta x}(k\Delta z))\int_{(k-1)\Delta z}^{k\Delta z}$$
$$(s13_{jq}(z)+is24_{jq}(z))dz$$ [Eq. 167]

FIG. 9 schematically shows the matrix representation of the operation of reconstruction of two-dimensional absorption profile $a_{xz}$.

The cost function associated with the reconstruction of vector $a_{xz}$ may have the same form as in the example of FIG. 5 (equation 42), with a fidelity term of same nature and a regularization term enabling to constrain the 2D reconstruction of the absorption of the medium.

Such a two-dimensional measurement principle has been disclosed for a synchronous detection mode with a demodulation in the electronic domain. It may however be easily adapted to a low-frequency acquisition mode with a demodulation in the optical domain, as described in relation with FIG. 6.

Further, this principle may be extended to three-dimensional measurements by adding an axis y, for example, orthogonal to axes x and z, and by using a two-dimensional array of ultrasound transducers and an activation function γ depending on x and y.

To increase the lateral resolution (in x and/or in y) of the measurement, an array, linear or not, of transducers may further be used and a simultaneous activation of overlapping sliding groups of a plurality of neighboring transducers may be provided.

It may further be provided to use different modulation functions Φ according to the activated transducers rather than a modulation function common to all transducers.

More generally, sub-groups of transducers according to the desired acoustic excitation form may be sequentially activated (according to variable directions, for example, in a given plane or volume), to increase the lateral resolution.

An acquisition model enabling to reconstruct the amplitude of the absorption profile $a_M$ of the object beam has been provided hereabove. This vector, which is a function of position z ($a_M(z)$), has now been considered as having a constant phase according to the index and the measurement position (that is, as if a single pixel measuring a static medium was considered).

Now noting:

$$a_M(z) = \rho(z)e^{i\theta^*(z)} \quad [\text{Eq. 168}]$$

it is desired to reconstruct the absorption profile $\rho$ which is a vector formed of real positive values in the range from 0 to 1.

Now considering an array of $n_v$ by $n_h$ pixels sampling speckle grains (that is, speckles of the interference pattern), $n_v * n_h$ different variants of coefficient $Y_j$ are simultaneously measured. Assuming that the signal received by each pixel has its own random phase $\theta$ uniformly distributed between 0 and $2\pi$, this provides a profile $a_M$ depending on index p of the pixel, that is:

$$a_M(p,z) = \rho(z)e^{i\theta^\wedge(p,z)} \quad [\text{Eq. 169}]$$

The measurement of coefficient $Y_j$ can thus be considered as a set of $n_v * n_h$ samples modeled by the scalar product of the transition matrices previously-defined with profile $a_M$ such that:

$$Y_j[p] = \langle (\mathcal{A}_{Re})_j, \text{Re}(a_M[p]) \rangle + \langle (\mathcal{A}_{Im})_j, \text{Im}(a_M[p]) \rangle \quad [\text{Eq. 170}]$$

$$Y_j[p] = \langle (\mathcal{A}_{Re})_j, \rho \odot \cos(\theta[p]) \rangle + \langle (\mathcal{A}_{Im})_j, \rho \odot \sin(\theta[p]) \rangle \quad [\text{Eq. 171}]$$

where symbol [Eq. 172] $\odot$ designates the point-to-point multiplication.

One thus has:

$$Y_j[p] = \langle (\mathcal{A}_{Re})_j \odot \cos(\theta[p]), \rho \rangle + \langle (\mathcal{A}_{Im})_j \odot \sin(\theta[p]), \rho \rangle \quad [\text{Eq. 173}]$$

$$Y_j[p] = \langle (\mathcal{A}_{Re})_j \odot \cos(\theta[p]) + (\mathcal{A}_{Im})_j \odot \sin(\theta[p]), \rho \rangle \quad [\text{Eq. 174}]$$

$$Y_j[p] = \langle \text{Re}((\mathcal{A}_{Re})_j \odot \cos(\theta[p]) + (\mathcal{A}_{Im})_j \odot \sin(\theta[p])), \rho \rangle + i\langle \text{Im}((\mathcal{A}_{Re})_j \odot \cos(\theta[p]) + (\mathcal{A}_{Im})_j \odot \sin(\theta[p])), \rho \rangle \quad [\text{Eq. 175}]$$

$$Y_j[p] = \langle \beta_{Re}[p], \rho \rangle + i\langle \beta_{Im}[p], \rho \rangle \quad [\text{Eq. 176}]$$

$$\beta_{Re\,j}[p] = \text{Re}((\mathcal{A}_{Re})_j) \odot \cos(\theta[p]) + \text{Re}((\mathcal{A}_{Im})_j) \odot \sin(\theta[p]) \quad [\text{Eq. 177}]$$

$$\beta_{Im\,j}[p] = \text{Im}((\mathcal{A}_{Re})_j) \odot \cos(\theta[p]) + \text{Im}((\mathcal{A}_{Im})_j) \odot \sin(\theta[p]) \quad [\text{Eq. 178}]$$

Considering that phase $\theta$ follows a uniform law between 0 and $2\pi$, the variance according to the pixel axis, noted $\text{Var}_p$, can be expressed as follows:

$$\text{Var}_p(\beta_{Re_j}) = \frac{\text{Re}((\mathcal{A}_{Re})_j)^2 + \text{Re}((\mathcal{A}_{Im})_j)^2}{2} \quad [\text{Eq. 179}]$$

$$\text{Var}_p(\beta_{Im_j}) = \frac{\text{Im}((\mathcal{A}_{Re})_j)^2 + \text{Im}((\mathcal{A}_{Im})_j)^2}{2} \quad [\text{Eq. 180}]$$

The following notations are then used:

$$\sigma_p(\beta_{Re_j}) = \sqrt{\frac{\text{Re}((\mathcal{A}_{Re})_j)^2 + \text{Re}((\mathcal{A}_{Im})_j)^2}{2}} \quad [\text{Eq. 181}]$$

$$\sigma_p(\beta_{Im_j}) = \sqrt{\frac{\text{Im}((\mathcal{A}_{Re})_j)^2 + \text{Im}((\mathcal{A}_{Im})_j)^2}{2}} \quad [\text{Eq. 182}]$$

$$\sigma_p(Y_j) = \langle \sigma_p(\beta_{Re,j}), \rho \rangle + i\langle \sigma_p(\beta_{Im,j}), \rho \rangle \quad [\text{Eq. 183}]$$

$$\hat{Y}_j = \langle \widetilde{\beta_{Re_j}}, \rho \rangle + i\langle \widetilde{\beta_{Im_j}}, \rho \rangle \quad [\text{Eq. 184}]$$

$$\hat{Y} = \widetilde{B_{Re}}\rho + i\widetilde{B_{Im}}\rho = (\widetilde{B_{Re}} + i\widetilde{B_{Im}})\rho \quad [\text{Eq. 185}]$$

A measurement model specifying that the variance of the signals measured by the p pixels for each acquisition j is a function of the previously-identified transition matrices is thus available. This model may be used to reconstruct the modulus $\rho$ of the absorption profile.

Various embodiments and variants have been described. Those skilled in the art will understand that certain features of these various embodiments and variants may be combined, and other variants will occur to those skilled in the art. In particular, the described embodiments are not limited to the mathematical formulas used in the present disclosure. More generally, the provided method is applicable for other forms of equations modeling the optical process. As an example, in the acquisition model discussed hereabove, an amplitude $a_M$ common to order $\omega L + \omega US$ and to order $\omega L - \omega US$ has been considered. As a variant, the model may be refined by considering a specific vector for each of the two orders.

Further, in the above-described examples, a single phase jump per acoustic modulation period $T_{US}$ is provided. As a variation, a number of phase jumps per period $T_{US}$ greater than 1 may be provided to improve the spatial selectivity during the reconstruction of the absorption profile.

Further, the above-described examples may be adapted by replacing the phase jumps applied by the modulation and demodulation devices with frequency jumps or amplitude jumps.

Further, in the above-described examples, term $a_{Mref}$ may be used to take into account, in the transition matrix, a possible lack of uniformity of the acoustic marking beam of the sample in the marking area.

The above-described absorption profile measurement methods may further be combined with a phase conjugation method to obtain a better signal-to-noise ratio. Each measurement is then performed in three steps:
1) Measurement of vector $Y_j$ by any adapted method, possibly a known method of the state of the art;
2) Extraction of the complex measurement phase $Y_j$ and then refocusing of the incident beam on the sample by phase conjugation, for example, by means of a device of the type described in application FR1903526 (B18214/DD19189) previously filed by the applicant; and
3) New measurement of vector $Y_{j+1}$ according to the above-described method.

In another variant, a series of measurements may be performed with a same pair of patterns $\Omega$ and $\Phi$ for each measurement, an analysis of the phase variation of the measurements being implemented to extract information relative to the observed medium. In particular, in free field, the phase variations may enable to detect motions along the beam axis, or also density variations of a diffusion medium (for example, fog). In a diffusion medium, phase variations may enable to detect possible motions of the diffusers in the medium (variations of the motions of platelets enabling to trace back heart rate information for example). The cost function will possibly be adapted accordingly (the regularization term weighted by coefficient $\lambda$ may apply to the modulus or the phase of the measurements).

Further, a learning of absorption patterns with patterns $\Omega$ and $\Phi$ may be provided to allow a direct detection of the absorption profiles from the measurements, without passing through the phase of reconstruction by minimization of the cost function.

It should further be noted that although, in the above-described embodiments, the modulation of the object light beam and, possibly, the modulation of the reference light beam, are performed by acoustic-optical modulation, the described embodiments are not limited to this specific case. More generally, any other light beam modulation method may be used, for example, Pockels-effect modulation methods. In particular, in the examples of FIGS. 6 and 7, acoustic-optical modulators MAO1 and MAO2 may be replaced with Pockels effect modulators. In this case, the modulation signal is an electric field and no longer an acoustic wave.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. An imaging system, comprising:
   a coherent light source delivering an object beam and a reference beam;
   a modulation device capable of modulating all or part of the object beam with a modulation signal;
   an image sensor arranged to receive an interference pattern resulting from a combination of the object beam and of the reference beam; and
   a device of demodulation of the modulated portion of the object beam,
   the imaging system being configured to, during a measurement phase:
   apply to the modulation signal, via the modulation device, a first pseudo-random sequence of jumps of a parameter selected among a phase, a frequency, and an amplitude of the modulation signal; and
   simultaneously apply to the modulated portion of the object beam, via the demodulation device, a second pseudo-random sequence of jumps of said parameter,
   wherein the first and second sequences of jumps of said parameter have non-correlated patterns.

2. The system according to claim 1, configured to, during an acquisition phase, implement M successive measurement phases, M being an integer greater than or equal to 2, and, at each measurement phase, acquire, via the image sensor, a value representative of a complex field of the modulated portion of the object beam.

3. The system according to claim 2, comprising an electronic processing circuit configured to implement a step of reconstruction, based on the M values acquired during the acquisition phase, of a set of L values representative of a light absorption at L different positions on an optical path of the modulated portion of the object beam, L being an integer greater than or equal to 2.

4. The system according to claim 3, wherein L is greater than M.

5. The system according to claim 4, wherein the modulation device comprises an acoustic-optical modulator placed on the optical path of the object beam upstream of a scene to be analyzed.

6. The system according to claim 1, wherein the modulation device is an acoustic-optical modulation device.

7. The system according to claim 6, wherein the modulation device comprises an ultrasound transducer, the modulation signal being an ultrasound wave applied by the ultrasound transducer to a portion of a sample to be analyzed, placed on the optical path of the object beam.

8. The system according to claim 7, wherein the modulation device comprises a plurality of ultrasound transducers arranged in an array, linear or not, and, during each measurement phase, the ultrasound modulation wave is emitted in fractions by the different transducers according to a pseudo-random function y.

9. The system according to claim 1, wherein the demodulation device is an electronic demodulation device integrated to the image sensor.

10. The system according to claim 1, wherein the demodulation device comprises an acoustic-optical modulator placed on the optical path of the reference beam, upstream of the image sensor.

* * * * *